(12) United States Patent
Weissman et al.

(10) Patent No.: US 9,867,852 B2
(45) Date of Patent: Jan. 16, 2018

(54) VIRAL INACTIVATED BIOLOGICAL MIXTURE

(71) Applicant: Omrix Biopharmaceuticals Ltd., Rehovot (IL)

(72) Inventors: Lior Weissman, Nes-Ziona (IL); Itai Podoler, Rehovot (IL); Israel Nur, Moshav Timmorim (IL); Tamara Byk-Tennenbaum, Kiryat Ono (IL)

(73) Assignee: Omrix Biopharmaceuticals Ltd., Rehovot (IL)

(*) Notice: Subject to any disclaimer, the term of this patent is extended or adjusted under 35 U.S.C. 154(b) by 0 days.

(21) Appl. No.: 14/134,033

(22) Filed: Dec. 19, 2013

(65) Prior Publication Data
US 2014/0179602 A1    Jun. 26, 2014

Related U.S. Application Data

(60) Provisional application No. 61/740,410, filed on Dec. 20, 2012.

(30) Foreign Application Priority Data

Dec. 20, 2012 (IL) ......................................... 223786

(51) Int. Cl.
| | |
|---|---|
| A61K 35/14 | (2015.01) |
| A61L 2/18 | (2006.01) |
| A61L 2/00 | (2006.01) |
| A61K 35/19 | (2015.01) |

(52) U.S. Cl.
CPC .............. *A61K 35/19* (2013.01); *A61L 2/00* (2013.01); *A61L 2/0005* (2013.01); *A61L 2/0088* (2013.01); *A61L 2202/22* (2013.01)

(58) Field of Classification Search
None
See application file for complete search history.

(56) References Cited

U.S. PATENT DOCUMENTS

| | | | |
|---|---|---|---|
| 4,789,545 A | 12/1988 | Woods et al. | |
| 5,094,960 A | 3/1992 | Bonomo | |
| 5,213,814 A * | 5/1993 | Goodrich et al. | 424/532 |
| 5,599,719 A * | 2/1997 | Woiszwillo | C07K 1/30 436/17 |
| 6,121,232 A | 9/2000 | Nur et al. | |
| 7,125,569 B2 | 10/2006 | Nur et al. | |
| 2010/0233149 A1* | 9/2010 | Lloyd et al. | 424/94.64 |
| 2011/0027257 A1* | 2/2011 | Burnouf et al. | 424/94.64 |
| 2012/0156306 A1 | 6/2012 | Weissman et al. | |

FOREIGN PATENT DOCUMENTS

| | | | |
|---|---|---|---|
| CN | 1752102 | 3/2006 | |
| CN | 101969985 | 2/2011 | |
| EP | 1060741 | 12/2000 | |
| EP | 1010435 | 11/2010 | |
| WO | WO 9833533 | 8/1998 | |
| WO | WO 1999/012571 | 3/1999 | |
| WO | WO 02095019 | 11/2002 | |
| WO | WO 2012/085910 | 6/2012 | |
| WO | WO 2013/176754 | * 11/2013 | 424/177.1 |

OTHER PUBLICATIONS

Highsmith, FA, Caple, M, Walthall, B, Shanbrom, E, and Drohan WN "Viral inactivation of vesicular stomatitis virus in normal human serum by cross-linked polyvinylpyrrolidone", The Journal of Infectious Diseases 1993, vol. 167, pp. 1027-1033.*
Royal Society of Chemistry. The Merck Index Online. https://www.rsc.org/Merck-Index/; accessed on Mar. 18, 2015.*
Bertrand-Duchesne, M. et al. "Epidermal Growth Factor Released from Platelet-Rich Plasma Promotes Endothelial Cell Proliferation in vitro", Journal of Periodontal Research, 2010, 45: pgs. 87-93.
Burnouf, P-A. et al. "A Novel Virally Inactivated Human Platelet Lystate Preparation Rich in TGF-B. EGF, and IGF, and Depleted of PDGF and VEGF", Biotechnology Applications Biochemistry, (2010) 56, pgs. 151-160.
Circular of Information: For the Use of Human Blood and Blood Components. Advancing Transfusion and Cellular Therapies Worldwide, revised Dec. 2009, pp. 1-59.
Guerrier, L. et al. "Specific Sorbent to Remove Solvent-Detergent Mixtures from Virus-Inactivated Biological Fluids", Journal of Chromatography B: Biomedical Applications, 664 (1995) pp. 119-125.
Hirsh, J. et al. "Heparin and Low-Molecular-Weight Heparin: The Seventh ACCP Conference on Antithrombotic and Thrombolytic Therapy", Chest Journal, 126, (3), Sep. 2004, pp. 188S-203S.
Intini, Giuseppe, "The Use of Platelet-Rich Plasma in Bone Reconstruction Therapy", Biomaterials (2009) pp. 1-11.
Johansson, L. et al. "Platelet Lysate: A Replacement for Fetal Bovine Serum in Animal Cell Culture?".Cytotechnology, 42: pp. 67-74, 2003.
Kanno, T. et al. "Platelet-Rich Plasma Enhances Human Osteoblast-Like Cell Proliferation and Differentiaton", American Association of Oral and Maxillofacial Surgeons, 2005, pp. 362-369.
Lacci, K.M. et al. "Platelet-Rich Plasma: Support for its Use in Wound Healing", Review, Yale Journal of Biology and Medicine, 83 (2010), pp. 1-9.
Machovich, R. et al. "Effect of Heparin on Thrombin Inactivation by Antithrombin-III", Biochem. J. (1978), 173, pp. 869-875.
McFarlane, R.M. et al. "The Design of a Pedicle Flap in the Rat to Study Necrosis and its Prevention", Plastic and Reconstructive Surgery, vol. 35, No. 2, pp. 177-182, (1965).
Salganicoff, L. et al. "Subcellular Fractionation of PIG Platelets", Biochimica et Biophysica Acta, 385, (1975) pp. 394-411.
Nurden, A. T. et al. "Platelets and Wound Healing", Frontiers in Bioscience, 13, pp. 3535-3548, May 1, 2008.

(Continued)

Primary Examiner — Michelle F Paguio Frising
(74) Attorney, Agent, or Firm — David R. Crichton

(57) ABSTRACT

The invention relates to a viral inactivated biological liquid or dry mixture and to its preparation. Principally, the invention relates, but is not limited, to a mixture derived from a platelet source.

22 Claims, 8 Drawing Sheets

(56) References Cited

OTHER PUBLICATIONS

Slezak, S. et al. "Platelet-Mediated Cytotoxicity; Role of Antibody and C3, and Localization of the Cytoxic System in Membranes", Journal Experimental Medicine, vol. 166, Aug. 1987, pp. 489-505.
Su, C.Y. et al. "A Virally Inactivated Functional Growth Factor Preparation from Human Platelet Concentrates", Journal compilation 2009 International Society of Blood Transfusion, Vox Sanguinis (2009) 97, pp. 119-128.
Sulpice, E. et al. "Cross-Talk Between the VEGF-A and HGF SIgnalling Pathways in Endothelial Cells", Biology of the Cell (2009), vol. 101 (9), pp. 525-539.
Highsmith, F. et al 'Iodine-Mediated Inactivation of Lipid- and Nonlipid-Enveloped Viruses in Human Antithrombin III Concetrate' Blood (1995) vol. 86, No. 2 pp. 791-796.
Kakudo et al. Proliferation-promoting effect of platelet-rich plasma on human adipose-derived stem cells and human dermal fibroblasts. Plast Reconstr Surg. Nov. 2008;122(5):1352-60).
Mazzucco et al. Not every PRP-gel is born equal. Evaluation of growth factor availability for tissues through four PRP-gel preparations: Fibrinet, RegenPRP-Kit, Plateltex and one manual procedure. Vox Sang. Aug. 2009;97(2):110-8).
Rughetti et al. Platelet gel-released supernatant modulates the angiogenic capability of human endothelial cells. Blood Transfus. Jan. 2008;6(1):12-17.
European Pharmacopaiea Assay Procedure (1997) p. 857-858.
Kenney, A. et al 'Practical Protein Chromatography' Methods in Molecular Biology vol. 11 p. 298-305. (1992).
International Preliminary Report re: PCT/IL2013/000096 dated Jun. 23, 2015.
International Search Report re: PCT/IL2013/000096 dated Apr. 11, 2014.

\* cited by examiner

| | Treatment | | | |
|---|---|---|---|---|
| | 1 | 2 | 3 | 4 |
| EC50 | 2.93 | 0.99 | 2.4 | 0.89 |
| $R^2$ | 0.95 | 0.96 | 0.94 | 0.94 |
| 95% Confidence Intervals EC50 | 1.8-4.75 | 0.69-1.42 | 1.43-4.02 | 0.59-1.32 |

| | Treatment | |
|---|---|---|
| | 1 | 2 |
| EC50 | 0.11 | 0.05 |
| R² | 0.92 | 0.97 |
| 95% Confidence Intervals EC50 | 0.065-0.17 | 0.037-0.068 |

|  | Treatment | |
|---|---|---|
|  | 3 | 7 |
| EC50 | 0.34 | 1.95 |
| R² | 0.99 | 0.97 |
| 95% Confidence Intervals EC50 | 0.3-0.39 | 1.54-2.47 |

VIRAL INACTIVATED BIOLOGICAL MIXTURE

FIELD OF THE INVENTION

Generally, the invention relates to a viral inactivated biological liquid or dry mixture and to its preparation. Principally, the invention relates, but is not limited, to a viral inactivated platelet extract and preparation thereof.

BACKGROUND OF THE INVENTION

Platelets are small, irregularly-shaped a-nuclear cells that play a fundamental role in hemostasis and healing. Platelets contain a complete array of pre-synthesized proteins, among which are signaling proteins, cytoskeletal proteins, membrane proteins and regulatory proteins. They are involved in key stages of tissue regeneration and healing processes at the site of injury, mainly due to the content of platelet granules comprising a multitude of bioactive molecules including growth factors (GFs), cytokines and chemokines.

Platelet growth factors such as platelet-derived growth factor (PDGF), transforming growth factor (TGF), basic fibroblast growth factor (bFGF), vascular endothelial growth factor (VEGF) and others are key players in all the following phases of the wound healing cascade: inflammatory, proliferative and remodeling phase.

Studies have shown that platelet derived growth factors stimulate angiogenesis, mitogenesis, cell proliferation, neutrophils and macrophages, collagen synthesis, wound contraction, extracellular matrix synthesis, epithelialization and chemotaxis.

Platelets are routinely used by transfusion e.g. to improve hemostasis. Recently, platelets are increasingly used in the form of Platelet Rich Plasma (PRP), also referred to as PRP gel, platelet gel, PRP-clot etc. Typically, PRP is an ex vivo preparation consisting of autologous platelets concentrated in a limited volume of plasma (Lacci K M, Dardik A. Platelet-rich plasma: support for its use in wound healing. Yale J Biol Med. 2010 March; 83(1):1-9).

For topical application, PRP is usually activated by the addition of thrombin and/or $CaCl_2$ resulting in the formation of fibrin gel by the interaction between thrombin (endogenous or exogenous) and fibrinogen. Upon activation, the platelets undergo active degranulation and release various mediators including GFs (Lacci K M, Dardik A, 2010). The use of PRP for injection currently comprises a small but rapidly growing segment of the market. The rationale for using PRP in soft and hard tissue augmentation is its potential to enhance tissue regeneration in non-healing injuries, accelerate wound maturity, vascularization and epithelialization, decrease scar formation, and reduce post operative complications and morbidity (Lacci K M, Dardik A, 2010).

Studies using activated PRP together with various cell types have shown that factors e.g. growth factors released from PRP can induce cell proliferation [(e.g. Kanno et al. Platelet-rich plasma enhances human osteoblast-like cell proliferation and differentiation. J Oral Maxillofac Surg. 2005 March; 63(3):362-9; Bertrand-Duchesne et al. Epidermal growth factor released from platelet-rich plasma promotes endothelial cell proliferation in vitro. J Periodontal Res. 2010 February; 45(1):87-93; Kakudo et al. Proliferation-promoting effect of platelet-rich plasma on human adipose-derived stem cells and human dermal fibroblasts. Plast Reconstr Surg. 2008 November; 122(5):1352-60), modulate the angiogenic capability of human endothelial cells (Sulpice et al. Cross-talk between the VEGF-A and HGF signalling pathways in endothelial cells. Biol Cell. 2009 September; 101(9):525-39; Rughetti et al. Platelet gel-released supernatant modulates the angiogenic capability of human endothelial cells. Blood Transfus. 2008 January; 6(1):12-7), and induce osteo-inductive properties (Intini G. The use of platelet-rich plasma in bone reconstruction therapy. Biomaterials. 2009 October; 30(28):4956-66)]. Moreover, activated PRP was found to support in vitro cell growth and maintained viability of a number of target cells including myelomas, hybridomas, hepatocytes, fibroblasts and epithelial cells, at a level comparable or superior to the level supported by fetal bovine serum (Johansson et al. Platelet lysate: a replacement for fetal bovine serum in animal cell culture? Cytotechnology. 2003 July; 42(2):67-74).

PRP and released growth factors are currently used in various surgical tissue regeneration procedures, predominantly in orthopedic and dental surgery (Nurden et al. Platelets and wound healing. Front Biosci. 2008 May 1; 13:3532-48). In orthopedic surgery PRP is used mainly for knee arthroplasty, lumbar spinal fusion, and in intervertebral disc degeneration (reviewed in Nurden et al, 2008). Dentistry and maxillofacial surgery PRP applications include mainly consolidation of titanium implants, maxillary sinus augmentation and bone remodeling (reviewed in Nurden et al, 2008). PRP is also increasingly used for tendon and ligament repair, facial plastic and reconstructive surgery, chronic skin wound healing, ophthalmology, facial nerve regeneration, as well as in cardiac and bariatric surgery (reviewed in Nurden et al, 2008).

However, a major disadvantage of the current use of autologous PRP and released factors resides in the lack of standardization. Of note, different manual, semi-automated and fully-automated systems for preparation of PRP are commercially available that differ in parameters such as preparation time, platelet yield and collection efficiency (Mazzucco et al. Not every PRP-gel is born equal. Evaluation of growth factor availability for tissues through four PRP-gel preparations: Fibrinet, RegenPRP-Kit, Plateltex and one manual procedure. Vox Sang. 2009 August; 97(2): 110-8).

Another important variable is the technique used for platelet activation [autologous, heterologous or recombinant thrombin, calcium chloride or batroxobin (Rozman P, Bolta Z. Use of platelet growth factors in treating wounds and soft-tissue injuries. Acta Dermatovenerol Alp Panonica Adriat. 2007 December; 16(4):156-65)], which can affect the efficiency of granule release and the amount of secreted GFs (Rozman P, Bolta Z, 2007). Moreover, since platelets are very sensitive to mechanical stress and changes in the surrounding environment, they may be activated and GFs may be released during processing, prior to the intended activation step (Mazzucco et al, 2009). This uncontrolled activation may further increase the variability in the composition of the final product when using different PRP preparation systems. Additionally, a major inherent weakness of autologous PRP preparation is that the platelets GFs content varies among individuals, and therefore may lead to sub-optimal results. Finally, the financial burden of dedicated machinery, disposable PRP processing kits, and the need for trained personnel, should be taken into consideration when working with autologous PRP.

Background art includes Su et al. "A virally inactivated functional growth factor preparation from human platelet concentrates". Vox Sang. 2009 August; 97(2):119-128; Burnouf et al. "A novel virally inactivated human platelet lysate preparation rich in TGF-beta, EGF and IGF, and depleted of PDGF and VEGF". Biotechnol Appl Biochem. 2010 Aug. 6; 56(4):151-60; and U.S. Patent Publication No. US 2012-0156306.

SUMMARY OF THE INVENTION

In one aspect, the invention relates to a method for preparing a viral-safe biological liquid mixture, the method comprising the following steps: providing a biological liquid mixture; carrying out a solvent detergent (S/D) viral inactivation treatment; contacting the S/D treated mixture with an amphiphilic polymer; removing the S/D by hydrophobic interaction chromatography (HIC) and/or by oil extraction; collecting a material comprising a flow through fraction from HIC and/or a liquid fraction from oil extraction; and subjecting the material to at least one more orthogonal viral inactivation treatment.

In one embodiment of the invention, the amphiphilic polymer is non-toxic.

Yet, in a further embodiment of the invention, the amphiphilic polymer is a hydrocarbon based surfactant.

Yet, in a further embodiment of the invention, the amphiphilic polymer has an average molecular weight in the range of about 3.5 to lower than about 40 kilodalton.

In one embodiment of the invention, the average molecular weight is about 30 kilodalton.

Yet, in a further embodiment of the invention, the hydrocarbon based surfactant is polyvinylpyrrolidone (PVP).

In one embodiment of the invention, the PVP has an average molecular weight of about 30 kilodalton (kDa).

In one embodiment of the invention, the HIC comprises the steps of: loading the S/D treated and polymer contacted mixture to HIC; washing with a solution comprising an organic solvent and/or a salt: and collecting a washed fraction.

In one embodiment of the invention, the organic solvent is ethanol.

In one embodiment of the invention, the salt is NaCl.

In a further embodiment of the invention, the at least one more orthogonal viral inactivation treatment comprises heat inactivation.

In one embodiment of the invention, the method further comprises a step of concentrating the material.

In one embodiment of the invention, the method is for preparing a viral-safe platelet extract, and the biological liquid mixture is a platelet-enriched fraction.

In one embodiment of the invention, the collected material comprises the HIC flow through fraction combined with the HIC washed fraction.

In another aspect, the invention relates to a viral-safe biological liquid mixture obtainable according to the method of the invention.

In one embodiment of the invention, the concentration of PVP K25 is in the range of 0.1% (w/w) to lower than 1% (w/w).

In certain embodiments of the invention, the concentration of PVP K25 is in the range of 0.1% (w/w) to 0.5% (w/w).

In one embodiment of the invention, the PVP K17, K25, K30 concentration in the viral-safe biological liquid mixture is in the range of 0.01-5% (w/w).

In certain embodiments of the invention, the biological liquid mixture is a platelet extract enriched with PDGF-AB, PDGF-BB, EGF, VEGF and/or bFGF.

In another aspect, the invention relates to a method for removing solvent-detergent (S/D) from a biological liquid mixture comprising the S/D, the method comprises the steps of: providing the mixture comprising the S/D; contacting the mixture with an amphiphilic polymer; removing the S/D from the mixture by hydrophobic interaction chromatography (HIC) and/or by oil extraction; and collecting a material comprising a flow through fraction from HIC and/or a liquid fraction from oil extraction.

In one embodiment of the invention, the amphiphilic polymer is non-toxic.

In one embodiment of the invention, the biological liquid mixture is a platelet-enriched fraction.

In another embodiment of the invention, the mixture comprises chemokines, cytokines, growth factors, trophic factors or a mixture thereof.

In one embodiment of the invention, the HIC comprises the steps of: washing with a solution comprising an organic solvent and/or a salt; and collecting a washed fraction.

In one embodiment of the invention, the amphiphilic polymer is a hydrocarbon based surfactant.

In one embodiment of the invention, the hydrocarbon based surfactant is polyvinylpyrrolidone (PVP).

In one embodiment of the invention, the organic solvent is ethanol.

In one embodiment of the invention, the salt is NaCl.

In one embodiment of the invention, the collected material comprises the flow through fraction combined with the wash fraction.

In one embodiment of the methods, the source is contacted first with the S/D and then with the amphiphilic polymer.

In some embodiments of the methods, the PVP concentration in the S/D treated source is in the range of about 0.01 to 0.9 mM, 0.01 to 0.3 mM, or 0.025 to 0.3 mM.

In some embodiments of the methods, the HPMC concentration in the S/D treated source is in the range of about 0.01 to 0.3 mM.

In some embodiments, the methods further comprise a step of drying the material, thereby resulting in a biological dry mixture.

In a certain aspect, it is disclosed a method for preparing a biological liquid mixture composition from a biological source. The method comprises the following steps: providing the source; providing PVP and/or HPMC; treating the source with a solvent detergent (S/D) to allow viral inactivation and with the PVP and/or HPMC; removing the S/D by contacting the treated source with a hydrophobic interaction chromatography (HIC) resin; and collecting a material comprising an unbound fraction from HIC.

In a certain aspect, it is disclosed a biological liquid mixture composition obtainable according to the disclosed methods.

In one embodiment, the composition comprises a PVP concentration in the range of about 0.07 to 6 mM, 0.07 to 2 mM, or 0.17 to 2 mM.

In another embodiment, the composition comprises a HPMC concentration in the range of about 0.07 to 1.5 mM.

In a certain aspect, it is disclosed a pharmaceutical composition comprising an amphiphilic polymer; a platelet derived protein selected from the group consisting of a chemokine, a growth factor, a cytokine, a trophic factor and a mixture thereof; and a pharmaceutically acceptable carrier, wherein the amphiphilic polymer is PVP at a concentration in the range of about 0.07 to 6 mM or HPMC at a concentration in the range of about 0.07 to 1.5 mM.

In addition, all figures comprise $R^2$ fit, median effective concentration (EC50), and 95% Confidence Intervals EC50 values calculated by GraphPad Prism software.

Figure 6:
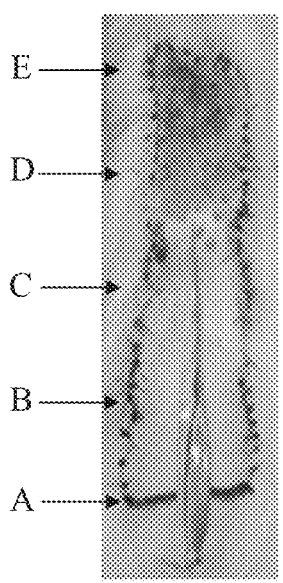

FIG. 6 shows a rat dorsal flap (3×10 cm) at 2 weeks after surgery performance. The flap was elevated in cranial to caudal direction. A, B, C, D and E indicate different areas from where samples were taken for histological analysis. A is closest to the caudal flap attachment and therefore heals best, whereas E is in the cranial end of the flap, which shows highest levels of necrosis (dark color). The abdominal and thoracic viscera were removed through ventral midline incision (line along the center of the flap).

Figure 7:
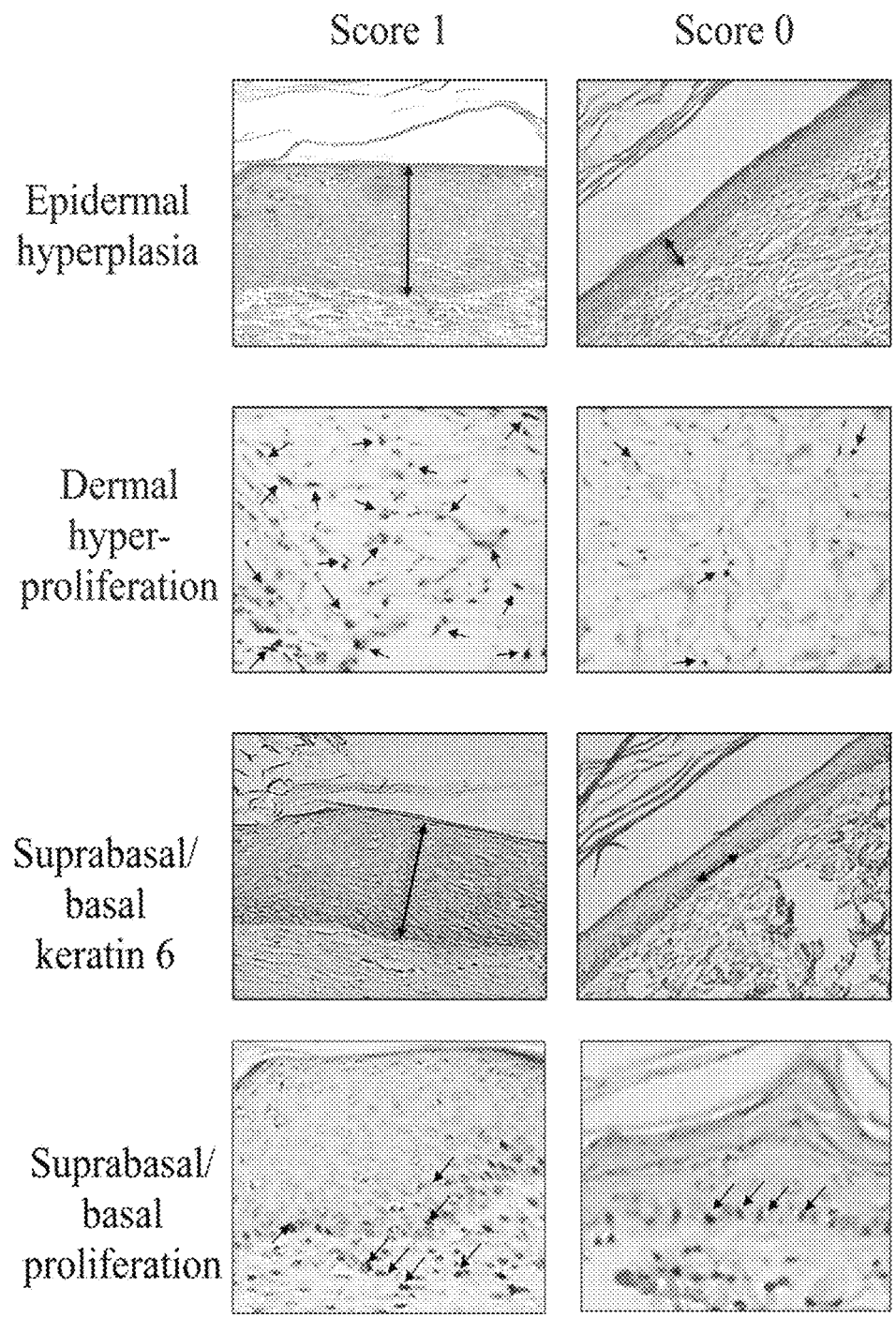

FIG. 7 shows typical staining patterns for normal and healing skin: H&E staining (epidermal hyperplasia, score 1 and epidermis after completed healing process, score 0). PCNA staining for dermal and epidermal proliferation (proliferating tissue, score 1 and normal tissue, score 0) and Keratin 6 staining (suprabasal staining, score 1, for healing and basal staining for regular skin, score 0).

Figure 8:
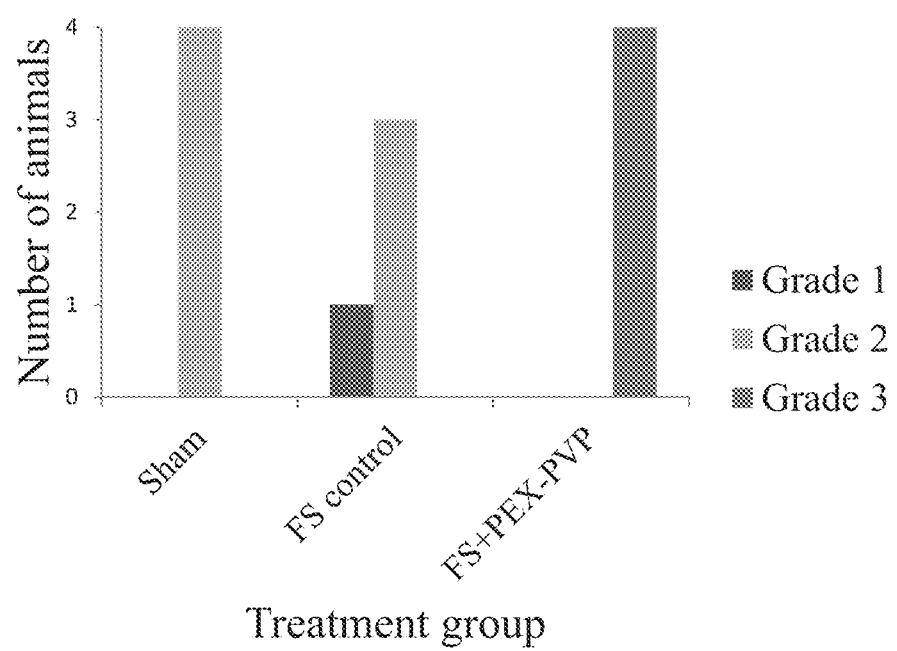

FIG. 8 shows the scores for the adherence grade of the rat dorsal flap after 2 weeks, as they were tested by gently pulling the flap in the area A-C (see FIG. 6) away from the wound bed using a tissue forceps. The attachment of the skin flap to the underlying tissue was compared to the attachment of normal areas of skin and graded 1 to 3 as follows: 1=no to low adherence, 2=below but nearly normal adherence or 3=about normal adherence between skin flap and underlying tissue.

DESCRIPTION OF SOME EMBODIMENTS OF THE INVENTION

The invention relates to methods for preparing a viral-safe biological liquid mixture such as a viral safe platelet extract. Platelets contain a complete array of factors involved in key stages of tissue regeneration and healing processes. Currently, whole autologous activated platelets (derived from the patient) are used for facilitating wound healing. However, there are multiple disadvantages of using whole autologous platelets, inter alia, the lack of standardization; the factors needed for healing may be scarce in the patient's own platelets; the special equipment needed for preparing the mixture of platelet factors; the procedure is time consuming and requires additional steps which are carried out on the patient itself; and the requirement of medically trained personnel. These problems can be solved e.g. by using a platelet extract prepared from multiple donors.

However, human blood-derived products may carry a risk of transmitting infectious agents such as viruses. Effective reduction of viral transmission risk can be achieved by including at least two orthogonal viral inactivation steps. Yet, including additional steps in the manufacture of a platelet extract may compromise the recovery and activity of the factors contained therein.

One of these methods of viral inactivation is "Solvent detergent (S/D) viral inactivation treatment".

This inactivation includes treatment with S/D and removal of the S/D. It was found according to the present invention that the recovery of certain growth factors is compromised after S/D removal by HIC.

It was found according to the present invention that recovery of certain platelet factors e.g. PDGF-AB; PDGF-BB; and bFGF, can be increased by contacting the S/D treated material prior to and/or during S/D removal with polyvinylpyrrolidone (PVP) or Hydroxy Propyl Methyl Cellulose (HPMC), which are non-toxic amphiphilic molecules.

It was found that contacting the S/D treated material with PVP and HPMC in accordance to the invention resulted in increased recovery or enrichment of PDGF-AB and other platelet factors e.g. PDGF-BB and bFGF.

These findings are surprising, in view that contacting the S/D treated material with heparin and low molecular weight heparin (both known to bind certain growth factors) during S/D removal increased the recovery of factors while contacting S/D treated material with PVP, which is a completely different compound (having amphiphilic characteristics) had a similar beneficial effect on growth factor recovery during S/D removal.

Also, the findings are surprising, since addition of PVP K30, K25, K17 and K12 under certain tested conditions did not compromise S/D removal.

It was found that using the method according to the invention to remove S/D from a source comprising platelet-derived mixture of factors results in high recovery of factors, high biological activity and efficient removal of S/D.

It was found that, using PVP K12, K17, K30 or PVP K25 during S/D removal increases recovery of platelets growth/trophic factors. It was found that the recovery using K30 was higher than using K25. The material obtained using PVP K25, and therefore comprising PVP K25, had a higher proliferative activity than material obtained using PVP K30 which comprised PVP K30.

The results also show that it is possible to reduce the PVP K25 concentration contacted with the platelet factors mixture to below 0.5% or 0.17 mM (thereby decreasing PVP to below 0.5% or 0.17 mM in the extract obtained after S/D removal) and still obtain an increase in factor recovery while maintaining the ability of HIC to efficiently remove S/D.

The results show that, the presence of different amounts of PVP K25, e.g. 0.1% (0.03 mM) and 0.5% (0.17 mM) in the extract did not affect its activity.

The results show that, unlike heparin and dextran sulfate at certain concentration, the presence of PVP in the final extract did not inhibit thrombin activity. This property of PVP is important especially when using fibrin sealant as a delivery agent for the platelet extract ("platelet extract" is one kind of biological liquid mixture composition).

The results show that growth factors recovery and activity in the presence of PVP K25 in large scale process are comparable with those in small scale.

These results suggest that PVP can be advantageously used during S/D removal in order to obtain a final extract having increased biological potency, provided that the type of PVP used and its concentration (e.g. w/w or molarity of PVP in the mixture) does not compromise the S/D removal.

In one embodiment, a platelet extract is obtained, after contacting a biological source with PVP in combination with ethanol and NaCl during an S/D removal step. The extract comprises PDGF-AB/TGF-β1; PDGF-AB/VEGF; TGF-β1/bFGF; and VEGF/bFGF ratios which are similar to the ratios in the Washed Aphaeresis Platelets Leukocyte-Reduced (WAP-LR) starting material and in the material prior to S/D removal.

These findings paved the way to prepare a biological liquid mixture composition according to the invention.

The method of the invention enables to prepare a platelet extract with increased recovery of cytokines, growth factors, chemokines and/or trophic factors following removal of S/D.

It is disclosed a method for preparing a viral-safe biological liquid mixture composition from a biological source, the method comprising the following steps: providing the source; providing an amphiphilic polymer, treating the source with a solvent detergent (S/D) to allow viral inactivation and with the amphiphilic polymer; removing the S/D by contacting the treated source with an hydrophobic interaction chromatography (HIC) resin; and collecting a material comprising an unbound fraction from HIC; wherein the method comprises at least one more orthogonal viral inactivation treatment, thereby obtaining the viral-safe biological liquid mixture composition.

In one aspect, the invention provides a method for preparing a viral-safe biological liquid mixture, the method comprising the following steps:
providing a source; carrying out a solvent detergent (S/D) viral inactivation treatment; contacting the S/D treated material with a non toxic amphiphilic polymer, removing the S/D by hydrophobic interaction chromatography (HIC) and/or by oil extraction; and subjecting the material to at least one more orthogonal viral inactivation treatment.

Examples of the source include, but are not limited to, body fluids such as blood; blood fractions, cryoprecipitate, cell cultures, lipophilic proteinaceous agents; cells, cell particles and/or cell organelles; cell lysate; platelet lysate; blood buffy coat; animal tissue extracts, such as bovine lungs, bovine intestines or animal bone extracts gelatin, bovine serum albumin, as well as animal derived water immiscible fats, such as lanoline. The source can be derived from a plurality of donors.

In one aspect it is disclosed a method for removing solvent-detergent (S/D) from a biological source comprising S/D, the method comprises the steps of: providing the source; providing an amphiphilic polymer; treating the source with S/D and with the amphiphilic polymer; removing the S/D from the biological source by contacting the treated source with an hydrophobic interaction chromatography (HIC) resin; and collecting a material comprising an unbound fraction from HIC.

In one embodiment the method of removing the S/D omits a further step of oil extraction.

It has been found that the method of the invention can be used to remove S/D in the absence of a step of oil extraction partition.

In one embodiment, the invention relates to a method for preparing a viral-safe platelet extract, the method comprising the following steps: providing a platelet-enriched fraction from more than one donor; carrying out a solvent detergent (S/D) viral inactivation treatment; contacting the S/D treated material with a non toxic amphiphilic polymer; removing the S/D; and subjecting the material to at least one more orthogonal viral inactivation treatment.

The term "platelet extract" refers to a biological mixture comprising platelet-derived factors. Typically, extracts are cell free.

In one embodiment, the method comprises preparing a platelet lysate. The term "lysate" refers to a solution produced when cells are destroyed by disrupting their cell membranes. Lysis of the platelets and release of the factors (e.g. various platelet growth factors and/or trophic factors) entrapped in the platelets, can be carried out by freezing and thawing the platelets enriched fractions, by S/D treatment, by sonication [Slezak et al., (1987) J. Exp. Med. V 166 p 489-505], by French press [Salganicoff et al., (1975) Biochem. Biophys. Acta v385 p 394-411] and/or by any other method known in the art.

In one embodiment of the invention, lysis of the platelets is carried out by freezing and thawing the platelets-enriched fractions followed by carrying out an S/D treatment. Typically, lysis of the platelets produces a cell free platelet lysate.

The term "viral-safe biological liquid mixture" refers to a mixture and/or composition which was subjected to at least two orthogonal viral inactivation treatments.

The term "viral-safe platelet extract" refers to an extract which was subjected to at least two orthogonal viral inactivation treatments.

The term "viral inactivation treatment" and "inactivating viruses" refers to a situation wherein viruses are maintained in the solution but are rendered non-viable e.g. by dissolving their lipid coat; and/or to the situation wherein viruses are physically removed from the solution e.g. by size exclusion techniques.

The term "orthogonal viral inactivation treatment" involves carrying out at least two different and independent treatments for inactivating viruses. A combination of two or more of the following non limiting treatment examples can be used: heat inactivation, Solvent/Detergent (S/D), nanofiltration, Low pH treatment, UV irradiation and Sodium thiocyanate treatment.

"Solvent detergent (S/D) viral inactivation treatment" typically refers to a process that inactivates enveloped or lipid-coated viruses by destroying their lipid envelope. The treatment can be carried out by the addition of detergents (such as Triton X-45, Triton X-100 or polysorbate 80) and solvents [such as tri(n-butyl) phosphate (TnBP), di- or trialkylphosphates]. The solvent-detergent combination used to deactivate lipid coated viruses may be any solvent-detergent combination known in the art such as TnBP and Triton X-100; polysorbate 80 and Sodium cholate and other combinations.

The concentration of the solvent(s) detergent(s) used can be those commonly used in the art, for example as carried out in U.S. Pat. No. 5,094,960A, U.S. Pat. No. 4,789,545A. In one embodiment of the invention, a combination of >0.1% TnBP and >0.1% Triton X-100 is used. In another embodiment of the invention, a combination of 1% Triton X-100 and 0.3% TnBP is used. Typically, the conditions under which the solvent-detergent inactivates the viruses consist of 10-100 mg/ml of solvent detergent at a pH level ranging from 5-8, and a temperature ranging from 2-37° C. for 30 minutes to 24 hours. However, other solvent detergent combinations and suitable conditions will be apparent to any person versed in the art. This inactivation includes treatment with S/D and removal of the S/D.

"Heat inactivation" typically refers to a process by which heat destroys both lipid-enveloped and non-enveloped viruses. "Heat inactivation" is interchangeable with the term "Pasteurization". The heat inactivation can be carried out at a temperature in the range of 59.5 to 60.5° C. for a period of 9 to 10.5 hours e.g. the inactivation can be carried out at 60° C. for 10 hours. Stabilizers such as sucrose and glycine can be added into the material during the heat inactivation step.

"Nanofiltration" typically refers to a process by which lipid-enveloped and non-enveloped viruses are excluded from the sample by using nanometer-scale filters such as Planova™ 20N, 35N and 75N; Viresolve/70™, Viresolve/180™. The filters can have a pore size of less than 70 nm, preferably between 15 and 50 nm. However, any membrane having a pore size sufficient to reduce or eliminate viruses from the sample can be employed in nanofiltration. Viruses removed by nanofiltration can be enveloped [e.g. HIV, hepatitis B virus, hepatitis C virus, West Nile Virus, cytomegalovirus (CMV), Epstein-Barr virus (EBV), herpes simplex virus], and non enveloped (e.g. hepatitis A virus, paravirus B 19, Polio virus).

Low pH treatment is typically effective against enveloped viruses. In one embodiment of the invention, the platelet lysate is subjected to a low pH, typically to a pH of 4, and lasts anywhere between 6 hours and 21 days. "Low pH treatment" is interchangeable with the term "acidic pH inactivation".

In one embodiment of the invention, the first viral inactivation step of the extract preparation comprises solvent-detergent (S/D) treatment of the platelets for eliminating enveloped viruses. The S/D treatment also promotes lysis of the platelets and release of their content into the solution. For optimal envelope viral inactivation, a sub-step including aggregates removal (e.g. by filtration) can be carried out during the S/D treatment step.

The term "platelet-enriched fraction from more than one donor" refers to a platelet-enriched material which is obtained from at least two individuals. The individuals can be human or other mammalians. In some embodiments, platelets are collected from 5 to 12 donors.

The term "platelet-enriched fraction" refers to a plasma composition having a concentration of platelets above that of the concentration of platelets normally found in blood. In a particular embodiment, platelet concentration is above the normal baseline concentration of platelets, for example, about 200.000 platelets/µL. For example, the platelet concentration may be at least 1.1, 1.2, 1.3, 1.4, 1.5, 1.6, 1.7, 1.8, 1.9, 2, 3, 4, 5, 6, 7, 8, 9, 10, 15, 20, 25, 30, 35, 40, 45, 50, 55, 60, 65, 70, 75, 80, 85, 90, 95, or 100 times or more the normal concentration in blood. In certain embodiments, the platelet-enriched fraction has a platelet concentration of greater than about 200,000 platelets/µL, 300,000 platelets/µL, 400,000 platelets/µL, 500,000 platelets/µL, 600,000 platelets/µL, 700,000 platelets/µL, 800,000 platelets/µL, 900,000 platelets/µL, 1,000,000 platelets/µL, 1,100,000 platelets/µL, 1,200,000 platelets/µL, 1,300,000 platelets/µL, 1,400,000 platelets/µL, 1,500,000 platelets/µL, 1,600,000 platelets/µL, 1,700,000 platelets/µL, 1,800.000 platelets/µL, 1,900,000 platelets/µL, or 2,000,000 platelets/µL.

Fractions from which the platelet-enriched material can be obtained from include, but are not limited to, blood fractions, plasma fractions, washed and leukocyte-reduced platelets from aphaeresis, and platelets from aphaeresis. In one embodiment, washed and/or leukocyte-reduced platelets pooled from multiple donors is used as the starting material for preparation of the platelet extract.

Using washed platelets as the starting material for preparing the extract enables obtaining a non-clottable platelet extract with reduced plasma impurities (e.g. reduced IgG and fibrinogen levels).

Typically, the term "platelet starting material" relates to platelet-enriched fractions obtained from more than one donor for use in the method of the invention. The platelet-enriched fractions can be, for example, separated from units of whole blood, from blood fractions and/or from plasma fractions. The platelet-enriched fractions can be obtained from aphaeresis donations. The starting material can be washed and/or leukocyte-reduced. In one embodiment of the invention, the platelet-enriched fractions are washed and leukocyte-reduced and are obtained from aphaeresis donations. In one embodiment, the minimal number of platelets in an aphaeresis leukocyte-reduced collected unit is about or more than $3.0 \times 10^{11}$ as specified in the "Circular of Information for the Use of Human Blood and Blood Components".

The term "washed platelets" refers to platelets which were subjected to a washing step. During the washing procedure there can also be losses of platelets. The washing can be carried out using 0.9% sodium chloride with or without small amounts of dextrose. The washing procedure can be carried out as elaborated in the "Circular of Information for the Use of Human Blood and Blood Components". In one embodiment of the invention, the washing is carried out as follows: a platelet material unit is centrifuged under gentle conditions. Then, the supernatant is discarded and the platelet pellet is washed at least twice (with centrifugation between the washes) with saline under gentle conditions. The washed and re-suspended platelets can be frozen until used in the method of the invention.

The term "leukocyte-reduced" refers to a content of leukocyte which is lower than the content of leukocyte in whole blood (content in whole blood is about 1 to $10 \times 10^9$ white cells per blood unit). Any leukocytes reduction methods, e.g. by filtration, can be used to obtain a leukocyte-reduced unit. The reduction in leukocytes can be carried out during aphaeresis. Typically, a leukocyte-reduced unit of platelets which contains less than about $5 \times 10^6$ leukocytes is used as the starting material for the preparation of the platelet extract.

The term "aphaeresis" typically refers to the withdrawal of blood from a single donor, with a portion (e.g. platelets) being separated and retained and the remainder retransfused into the donor. One unit of aphaeresis platelets obtained from a single donor can contain about or higher than $3.0 \times 10^{11}$ platelets. In one embodiment of the invention, one unit of aphaeresis platelets obtained from a single donor contains up to $6.0 \times 10^{11}$ platelets. Oftentimes, when there are more than $6 \times 10^{11}$ platelets in one donation, the donation unit is split into two separate bags.

The term "amphiphilic polymer" or "amphipathic polymer" is a polymer possessing both hydrophilic (having an affinity for water, polar) and lipophilic (having an affinity for lipids) properties. The lipophilic group is typically a large hydrocarbon moiety, such as a long chain of the form $CH_3(CH_2)_n$, with $n > 4$. In one embodiment, the hydrophilic group falls into one of the following categories:

1. Charged groups:
   Anionic. Examples, with the lipophilic part of the molecule represented by an R, are:
   carboxylates: $RCO_2-$;
   sulfates: $RSO_4-$;
   sulfonates: $RSO_3-$.
   phosphates: The charged functionality in phospholipids.
   Cationic. Examples:
   amines: $RNH_3+$.

2. Polar, uncharged groups. Examples are alcohols with large R groups, such as diacyl glycerol (DAG), and oligo-ethyleneglycols with long alkyl chains.

Often, amphiphilic species have several lipophilic parts, several hydrophilic parts, or several of both. Proteins and some block copolymers are such examples.

Amphiphilic compounds have lipophilic (typically hydrocarbon) structures and hydrophilic polar functional groups (either ionic or uncharged).

As a result of having both lipophilic and hydrophilic portions, some amphiphilic compounds may dissolve in water and to some extent in non-polar organic solvents. When placed in an immiscible biphasic system consisting of aqueous and organic solvent the amphiphilic compound will partition in the two phases. The extent of the hydrophobic and hydrophilic portions determines the extent of partitioning.

Non limiting examples of non toxic amphiphilic polymers are Polyethylene glycol (PEG), polyethylene oxides (PEO), Poly(2-acrylamidohexadecylsulfonic acid (PAMC16S), lipopoly(2-methyl-2-oxazoline)s (LipoPOxs), Hydroxyethyl starch (HES), amphiphilic polymers derived from Tris(hydroxymethyl)-acrylamidomethane (THAM) Cationic polymers used for gene therapy like Poly-L-Lysin (PLL)- and Polyethyleneimine (PEI)-based polymers.

Typically the term "non toxic" refers to a product, substance, or chemical compound that is non-toxic to a patient at the dosages and concentrations employed, and will not cause adverse health effects, either immediately or over the long-term. A non-toxic or physiologically safe compound is understood as a compound with an LD50 (rat) of ≥500 mg/kg, better ≥950 mg/kg and best ≥2000 mg/kg.

In one embodiment of the invention, the amphiphilic polymer is a hydrocarbon based surfactant.

The term "hydrocarbon based surfactant" is hydrocarbon compound that lowers the surface tension of a liquid, the interfacial tension between two liquids, or that between a liquid and a solid. Hydrocarbon surfactants may act as detergents, wetting agents, emulsifiers, foaming agents, and dispersants.

The term "contacting" is used herein in its broadest sense and refers to any type of combining action which e.g. brings the amphiphilic polymer into sufficiently close proximity with the factors of interest present (e.g. growth factors, cytokines, chemokines and/or trophic factors) in the S/D treated material or source such that a binding interaction will occur between the amphiphilic polymer and the factors. Contacting includes, but is not limited to, mixing, admixing and/or adding the amphiphilic polymer into the S/D treated material and/or adding the amphiphilic polymer into the buffer used to wash the HIC column, and/or in the oil used to extract the S/D.

The polymer can have an average molecular weight of from 200 to below 50000 Daltons. In one embodiment of the invention, the amphiphilic polymer is polyvinylpyrrolidone (PVP). PVP can be in a range of 12-30K, or about 12, 13, 14, 15, 16, 117, 18, 19, 20, 21, 22, 23, 24, 25, 26, 27, 28, 29, 30K.

In one embodiment of the invention, the amphiphilic polymer is polyvinylpyrrolidone having an average molecular weight in the range of 3500 to 40000 Dalton. E.g. the PVP used can have an average molecular weight of 3500 Dalton and/or a K-Value in the range of 10.2-13.8; an average molecular weight of 8000 Dalton and/or a K-Value in the range of 16.0-18.0; an average molecular weight of 30000 Dalton and/or a K-Value in the range of 22.5-27.0; or an average molecular weight of 40000 Dalton and/or a K-Value in the range of 27.0-32.4. A combination of different amphiphilic polymers and/or the same polymer having a different average molecular weight can be used to contact the S/D treated material. In one embodiment, PVP having an average molecular weight of 30000 Daltons is added into the S/D treated material prior S/D removal e.g. prior to loading the material onto the column; and then PVP having a molecular weight of 30000 Daltons is added into the buffer used to wash the column.

It was found that PVP K25 concentration of (0.3 mM) 1% or higher resulted in the presence of S/D material, namely Triton X-100, in the post-SDR material above the acceptable limit.

In one embodiment of the invention, the amphiphilic polymer is contacted with the S/D treated material within a concentration range of 0.01% (w/w) to lower than 1% (w/w); in the range of 0.1% (w/w) to lower than 1% (w/w); or in the range of 0.1% (w/w) to 0.5% (w/w).

In a next step, an S/D removal step is carried out. The term "solvent-detergent removal (S/D removal)" refers to the removal of the bulk of the solvent-detergent used in the S/D treatment. The removal of solvent-detergent comprises using hydrophobic interaction chromatography column (HIC) e.g. C-18 silica packing material and SDR (Solvent-Detergent removal) HyperD; oil extraction; a combination thereof or any other method known in the art.

In one embodiment of the invention, oil extraction is used to remove the solvent-detergent.

Liquid-liquid extraction, also known as "solvent extraction" and "partitioning", or "depletion partition" is a method to separate compounds based on their relative solubilities in two different immiscible liquids. It is an extraction of a substance from one liquid phase into another liquid phase. Two immiscible liquids can be oil and an aqueous liquid. Oftentimes in this case removal of a substance using oil and aqueous partition is referred as "oil extraction". Addition of oil to an aqueous solution comprising solvent detergent, mixing and allowing partition between water and oil will lead to leave a major part of the solvent detergent in the oil phase.

In another embodiment of the invention. SDR HyperD, which is a chromatographic packing made of silica beads in which the pore volume is filled with a three-dimensional cross-linked hydrophobic acrylic polymer, is used to remove the solvent-detergent. The SDR HyperD advantageously involves a mixed-mode adsorption of hydrophobic interaction and is associated with a molecular exclusion effect [Guerrier L et al. "Specific sorbent to remove solvent-detergent mixtures from virus-inactivated biological fluids". J Chromatogr B Biomed Appl. 1995 Feb. 3; 664(1):119-125].

The term "hydrophobic interaction chromatography (HIC)" refers e.g. to a column packed with a hydrophobic polymer resin. Generally the mixture is allowed to travel through the column comprising the packed resin at a certain flow rate, and the S/D material is being removed. HIC can be carried out batch-wise.

Hydrophobic resins are well known in the art. Non limiting examples are e.g. C-18 silica packing material and SDR (Solvent-Detergent removal) HyperD.

The hydrophobic interaction chromatography can be carried out by a method comprising the following steps: loading the S/D-treated and polymer-contacted material to HIC; washing with an aqueous solution optionally comprising a low concentration of organic solvent (e.g. ethanol at a concentration range of 5-15%) and/or a salt (e.g. NaCl at a concentration of 0.2-1.2M); and collecting the wash material.

Non limiting examples of salts are KCl, $MgCl_2$, $CaCl_2$ and the like.

Non limiting examples of organic solvents are isopropanol, glycerol, ethylene glycol and the like.

The term "loading to HIC" refers to applying the material to the column. However, if desired, the same resin can be used "batch-wise" to remove the S/D material. As used herein, "batch-wise" generally refer to a technique in which the resin and the mixture are incubated together e.g. in a stirred tank, batch reactor or a vessel, and the adsorption is carried out in a continuous manner. In one embodiment of the invention, the mixture is contacted with the resin in a vessel e.g. a tube, and after an incubation period, the vessel is centrifuged and the supernatant comprising the platelet-derived factors is collected (the S/D material is present within the precipitate). The batch method can be carried out in a vessel or a batch reactor.

The term "S/D-treated and polymer-contacted material" means a substance that was subjected to an S/D for viral inactivation and contacted with an amphiphilic polymer as defined above.

The material loaded to the HIC column can be dissolved in a binding buffer. The column can be equilibrated prior to loading the material e.g. by washing the column with the binding buffer.

The term "equilibrate" refers to allowing and/or adjusting the column to reach a specific buffer condition such as a specific pH level, specific amphiphilic polymer concentration and ionic strength. In one embodiment of the invention, the adjustment of the column is carried out by washing the column with an equilibration buffer having a predetermined pH level and ionic strength prior to loading the S/D-treated and polymer-contacted material onto the column. In one embodiment of the invention, the equilibration buffer comprises 20 mM sodium acetate and 10 mM glycine at pH 6.8-7.4; 0.2% (w/w from the total volume) human serum albumin (HSA) and 0.1% amphiphilic polymer.

In one embodiment of the invention, a method for removing solvent-detergent (S/D) from a biological liquid mixture comprises the steps of: contacting the S/D treated mixture with a non toxic amphiphilic polymer; removing the S/D from the mixture by subjecting the mixture to hydrophobic interaction chromatography (HIC) and/or oil extraction and collecting a material comprising a flow through fraction from HIC and/or liquid fraction from oil extraction.

In a further embodiment, the HIC comprises the steps of: washing with a solution comprising organic solvent and/or a salt.

In a further embodiment of the invention, the collected material includes the flow through fraction combined with the wash fraction of HIC.

The term "binding buffer" refers to the buffer used during loading of the S/D-treated and polymer-contacted material onto the chromatography column. Oftentimes, the equilibration buffer used to adjust the column prior and/or during loading of the material is termed binding buffer. In one embodiment of the invention, the binding buffer comprises 20 mM sodium acetate and 10 mM glycine at pH 6.8-7.4; 0.2% (w/w from the total volume) human serum albumin (HSA) and 0.1% amphiphilic polymer. HIC can also comprise the steps of: washing HIC with the equilibration buffer and/or the binding buffer, and collecting an unbound material.

Flow through or unbound material typically refers to the fraction collected following washing of the loaded column with the same buffer used for equilibration and/or the buffer used for loading the mixture onto the column ("binding buffer").

The term "washing" refers to washing the column during an S/D removal step with a solution or condition equal or different from the solution or condition used to load and/or equilibrate the column, and/or equal or different from the solution used in a previous step. The washing conditions are such that S/D substantially remains bound to the column/resin whereas the factors are washed/unbound.

Washing conditions, may involve an increase in salt concentration and/or including an organic solvent within the solution.

The platelet extract may comprise a mixture of growth factors, trophic factors, chemokines and/or cytokines.

The term "growth factor" typically refers to an agent that promotes cellular growth, proliferation and/or differentiation. Examples of growth factors include, but are not limited to, transforming growth factor (TGF) e.g. TGF-b1, fibroblast growth factor (FGF) e.g. bFGF, vascular endothelial growth factors (VEGF), platelet-derived growth factor (PDGF) e.g. PDGF-AB, and the like.

The term "trophic factors" typically refers to an agent that stimulates differentiation and/or survival of cells. Examples of trophic factor include, but are not limited to, adhesion molecules, bone morphogenetic proteins, cytokines, eph receptor tyrosine kinase, epidermal growth factors, fibroblast growth factors (FGF), GDNF, heparin-binding growth factors, insulin-like growth factors, neurotrophins, semaphorins, transforming growth factors (TGF) β, tyrosine kinase receptor ligands, and the like.

The term "cytokines" typically refers to cell derived signaling protein molecules that are secreted by cells and are a category of signaling molecules used extensively in intercellular communication. Immune cells release cytokines.

A platelet factor may have a growth activity, a cytokine, a chemokine activity and/or a trophic activity.

In another aspect, the invention relates to an active and viral-safe (at least double viral inactivated) platelet extract derived from multiple donors obtainable according to the methods of the invention; and to its use. The viral-safe platelet extract comprises a mixture of biologically active platelet cell growth factors, chemokines, cytokines and/or trophic factors.

In another aspect, the invention relates to a method for removing an amphiphilic toxic molecule such as solvent-detergent (S/D) from a biological liquid mixture comprising the amphiphilic toxic molecule. The method comprises the steps of providing the biological liquid mixture comprising the amphiphilic toxic molecule; contacting the mixture with a non toxic amphiphilic polymer such as PVP; and removing the amphiphilic toxic molecule from the mixture.

An amphiphilic toxic molecule typically includes, but is not limited to, Triton X-45, polysorbate (e.g. polysorbate 20, polysorbate 80), Brij (polyethylene glycol lauryl ether, e.g. Brij 30, Brij 35, Brij 58), IGEPAL (octylphenoxypolyethoxyethanol. e.g. IGEPAL CA-630) and the like.

The term "biological liquid mixture" refers to any type of liquid substance obtained from a biological source and/or a liquid that comprises recombinant ingredients and/or recombinant platelet derived factors e.g. chemokines, growth factors, cytokines trophic factors or a combination thereof. "A biological source" typically includes, but is not limited to, preparations obtained from body fluids such as whole blood plasma or blood fractions e.g. cryodepleted plasma, cryoprecipitate, plasma or serum; semen; sputum; feces; sweat; saliva; nasal mucus; cerebrospinal fluid; a platelet derived fraction such as Platelet Rich Plasma releasate PRP-R (PRP-releasate); and urine, as well as liquids obtained from cell cultures, containing biological substances secreted by the cells into the preparation, or containing substances which originally were present inside the cells, and were released to the liquid preparation due to various manipulations such as lysing of the cells or activating of the cells.

The term "cryoprecipitate" refers to a blood component which is obtained from frozen plasma prepared from whole blood. A cryoprecipitate can be obtained when frozen plasma is thawed in the cold, typically at a temperature of 0-4° C., resulting in the formation of precipitated supernatant that contains fibrinogen and factor XIII. The precipitate can be collected, for example by centrifugation. The solution of BAC comprises further Factor VIII, fibronectin, von Willebrand factor (vWF), vitronectin, etc. for example as described in U.S. Pat. No. 6,121,232 and WO9833533.

In one embodiment, the method for removing S/D according to the invention can be used after a process for viral inactivation of a biological liquid preparation. Biologically derived liquid preparations such as blood and plasma preparations are used as raw materials from which a plurality of biologically useful compounds can be purified. Examples of such compounds include immunoglobulin, factor VIII, albumin, a 1 anti trypsine, Factor IX, factor XI, PPSB, fibrinogen, and thrombin (prothrombin). In addition, various biological products such as hormones, growth factors, enzymes, ligands and antibodies are isolated from biological preparations obtained from cell cultures.

Yet, in another aspect, the invention relates to a pharmaceutical composition comprising PVP at a concentration range of 0.07 to 6 mM and a platelet derived protein composition comprising chemokines, growth factors, cytokines, trophic factors or a mixture thereof.

It is shown here that performing removal of S/D using PVP in concentration of 0.9 mM (6 mM in the final product) resulted in removal of 98% of the triton to a final concentration of 170 ppm. The traces of Triton X-100 that remained in the material after the column were removed in the downstream process until no traces of triton were detected in the final product. Considering these results using PVP in concentration higher than 0.9 mM may result in elution of triton from the column at concentration that cannot be removed downstream.

The term "pharmaceutical composition" refers to any compound or composition of matter or combination of constituents, which when administered to a subject induces a physiologic and/or biological effect (e.g. induction of cell proliferation, cell motility, cell-cell interactions, and/or cellular morphological changes) by local and/or systemic action.

It was found that using PVP K12 and PVP K25 during S/D removal it is possible to obtain a composition which has ratios of the factors which are comparable to the ratios in the WAP starting material.

It is disclosed a composition having PDGF-AB/TGF-β1 in the range of about 0.3-0.4; PDGF-AB/VEGF in the range of about 41 to about 102; TGF-β1/bFGF in the range of about 1500 to about 1700; and/or VEGF/bFGF in the range of about 6.0 to 12.5.

The term "subject", as used herein, includes animals of mammalian origin, including humans. In one embodiment, the subject is a human.

The viral-safe platelet extract prepared according to the invention can be used for any therapeutic purpose.

The extract of the invention is suitable for any therapeutic use e.g. for promoting healing of injured tissue in a subject. The platelet extract can be used as is for injection into a target area or for intravenous administration; applied onto/administered into bandages, foams, pads and matrices and/or can be used in combination with fibrin sealant for topical applications. The extract can be released into/onto a desired location from different delivery agents such as bandages, pads, foams and matrices. The agents can be made of natural and/or synthetic materials. Examples of such materials include, but are not limited to, polymers, hydrogels, Polyvinyl alcohol (PVA), polyethylene glycol (PEG), hyaluronic acid, chondroitin sulfate, gelatin, alginate, collagen matrices, carboxymethylcellulose, dextran, poly(2-hydroxyethylmethacrylate) [PHEMA], agar, oxidized regenerated cellulose (ORC), self assembled peptides [SAPs], poly(glycolic) acid, poly(lactic) acid, fibrin and combinations thereof.

It was found that administering fibrin sealant in combination with a platelet extract obtained according to the invention which comprises PVP had a significant positive effect on healing in-vivo: it promoted skin flap adherence, and accelerated the healing process, as shown using histology, compared to fibrin sealant alone or the sham group (animals that underwent the same flap creation procedure, but did not have any treatment applied prior to flap closure).

The term "any therapeutic purpose" refers to any curative or preventive treatment; for cosmetic use; and/or for any disease, disorder or condition in a subject. Exemplary therapeutic purposes include, but are not limited to, to improve graft integration; accelerating internal or external wound healing. i.e., causing the wound to heal rapidly as compared to an untreated wound or to other known wound treatments; treating any injury or condition that requires stimulating angiogenesis, mitogenesis, cell proliferation, neutrophils and macrophages, collagen synthesis, migration, wound contraction, extracellular matrix synthesis, epithelialization and chemotaxis; injury or condition that requires tissue generation, regeneration or reorganization, epithelialization, formation of new blood vessels, or angiogenesis; for decreasing scar formation; reducing post operative complications and morbidity; for healing soft tissue e.g. skin wounds e.g. for healing surgical skin flap failure, cuts or ulcers. The composition disclosed can be administered by topical or parenteral route.

The platelet extract can be used in various surgical fields such as, but not limited to, orthopedic surgery (e.g. bone repair, articular cartilage repair, knee arthroplasty, lumbar spinal fusion, and in intervertebral disc degeneration); dental surgery; dentistry and maxillofacial surgery (e.g. consolidation of titanium implants, maxillary sinus augmentation and bone remodeling); for muscle, tendon and ligament repair; facial plastic and reconstructive surgery; chronic skin wound healing, skin burn healing, ophthalmology; facial nerve regeneration, peripheral nerve repair, central nervous system (CNS) repair (spine and/or brain surgery), optic nerve repair, nerve compression syndrome repair, cranial nerve repair, sciatic nerve repair; cardiac; gastrointestinal surgery and bariatric surgery. The extract can be administered onto a surface of a body part of a patient. The term "surface" refers to an external surface that can be seen by unaided vision and to a surface of an internal body part which is a part of the internal anatomy of an organism. External surfaces include, but are not limited to, the skin of the face, throat, scalp, chest, back, ears, neck, hand, elbow, hip, knee, and other skin sites. Examples of internal body parts include, but are not limited to, body cavity or anatomical opening that are exposed to the external environment and internal organs such as the nostrils; the lips; the ears; the genital area, including the uterus, vagina and ovaries; the lungs; the anus; the spleen; the liver; the cardiac muscle, and the gastrointestinal tract. The surface can be a bleeding or a non-bleeding site. Alternatively, the extract can be administered by injection e.g. intradermally, intraperitonealy, subcutaneously, intrathecally, intrasternally, intracranially, intramuscularly, and/or intravenously. The extract can also be administered by infusion.

The invention also provides a method of treating inflammation; tissue healing; organ reconstruction and/or tissue regeneration comprising administering to a subject in need a therapeutically effective amount of an extract according to the invention.

The extract according to the invention can also be used for facilitating growth, proliferation, differentiation and/or maintenance of various cell types e.g. stem cells. For this purpose, the extract can be used alone or in combination with fibrin sealant in in vivo and/or in vitro applications. In one embodiment, the extract can be used together with a biocompatible implant e.g. for tissue engineering in vivo, as well as for in vitro cell culturing.

The term "a therapeutically effective amount" refers to the dose required to prevent or treat (relieve a symptom or all of the symptoms) a disease, disorder or condition. The effective amount can be measured based on any change in the course of the disease in response to the administration of the composition. The effective dose can be changed depending on the age and weight of the subject, the disease and its severity (e.g. early or advanced stage) and other factors which can be recognized by the skilled in the art. The extract can also comprise a pharmaceutically acceptable excipient. As used herein the term "excipient" refers to an inert substance which is added into the extract. Typically, an excipient is a material used in the final formulation of a pharmaceutical composition. The excipients can be added, for example, in order to ensure that the active substances retain their chemical stability and/or biological activity upon storage, to aid the manufacturing process and/or for aesthetic reasons e.g. color. The added excipient is generally safe and non-toxic.

The platelet extract according to the invention can be used in combination with a surgical sealant. Different types of surgical sealants can be used in combination with the platelet extract, including, but not limited to, a biological sealant (such as a fibrin sealant prepared with fibrinogen and thrombin components); a synthetic sealant such as acrylates, cyanoacrylates, and polyethylene glycol (PEG) polymers; and a semisynthetic sealant e.g. made from a combination of biological and synthetic materials such as gelatin-formaldehyde-resorcinol (GFR) glue. In one embodiment of the invention, the platelet extract is used in combination with fibrin sealant components. In another embodiment of the invention, the platelet extract is used with a synthetic sealant.

If desired, the platelet extract obtained by the method of the invention can be dried e.g. by lyophilization, supercritical fluid technology, spray freeze drying, spray coating, modifications of spray coating such as drying with conventional spouted bed, and other drying methods based on solvent evaporation without atomization (such as vacuum drying, Xerovac1, foam drying, film drying) or spray drying. Prior to drying, the extract can be formulated with a cryoprotectant.

The term "cryoprotectant" refers to a substance which is added to solutions in order to retain the chemical stability and/or biological activity of the active components (e.g. growth factors, chemokines, cytokine and/or trophic factors) during freezing. Non limiting examples of cryoprotectant include, but are not limited to, carbohydrates such as Monosaccharides: include glucose (dextrose), fructose (levulose), galactose, and ribosedisaccharides Disaccharides: sucrose, lactose, maltose and trehalose and Disaccharides oligosaccharides another group are the poliols Sugar alcohols: Maltitol, Mannitol, sorbitol, xylitol and isomalt. Apart of carbohydrates other polymers such as Polyethylene glycol (PEG) can also be used as cryoprotectants such as polyethylene oxide (PEO) or polyoxyethylene (POE), or amino acids and polyamines.

The term "lyophilization" typically refers to the process of freezing a substance and then reducing the concentration of water e.g. by sublimation to levels which do not support biological or chemical reactions. The resulting lyophilized biological material may be stored for a relatively long period of time. Following storage, the lyophilized material can be used as a powder or can be reconstituted by the addition of various volumes of an aqueous solution. The volume added during reconstitution can be similar to the volume of the solution before lyophilization, lower (resulting in a concentration of the extract compared to the volume of the starting material) or higher (resulting in a dilution of the extract compared to the volume of the starting material). If desired, the platelet extract can be kept frozen or as solid e.g. lyophilized for prolonged storage or for use as a powder.

For example, the platelet extract obtained by the method of the invention can be kept frozen e.g. at −18° C. or at lower temperature, or as solid (e.g. lyophilized) for prolonged storage. The platelet extract can also be refrigerated e.g. at a temperature of 2° C. to 8° C.

The lyophilized extract can be used as solid or can be reconstituted in a pharmaceutically acceptable carrier prior to use. The term a "pharmaceutically acceptable carrier" refers to any diluent and/or a vehicle which is suitable for human administration or for animal administration. The carrier can be selected from any of the carriers known in the art such as, but not limited to, saline, sodium chloride solution, lactated ringers (LR), 5% dextrose in normal saline, and water for injection. If administered with fibrin sealant, the extract can be reconstituted in one of the sealant components (thrombin or fibrinogen) or can be reconstituted separately in another diluent or vehicle.

Of advantage, the lyophilization cycle and the formulation can allow for a very fast reconstitution of the extract e.g. within fibrin sealant e.g. to facilitate hemostasis and healing which calls for an emergency use, thus in this case the reconstitution is beneficially done within seconds. In one embodiment of the invention, albumin is used in the formulation to allow fast reconstitution.

The extract obtained according to the method of the invention can be concentrated. The concentration can be carried out at any step e.g. immediately after the S/D removal step or at a later step. Concentration can be achieved by diafiltration of the material and/or reconstitution of a lyophilized extract in a lower volume compared to the volume of the extract prior to its lyophilization.

The invention provides a kit. The kit may comprise a recipient comprising the extract according to the invention. The extract can be in a solid form e.g. lyophilized, as a solution or in frozen form. In the case that the extract is provided in solid form, the kit can further comprise a recipient with a pharmaceutically acceptable carrier for reconstituting the solid extract. The kit may further comprise one or more syringes and/or syringe needles for injecting the extract to the patient. The kit can comprise instructions for use. The instructions may describe how to administer the extract to a patient. The invention also relates to a kit comprising recipients containing the components of the fibrin sealant, the synthetic sealant, and/or another possible delivery agent; a recipient containing the extract of the invention; and instructions for use. Optionally, the extract of the invention can be in the recipient of one component of the fibrin sealant. Also, the invention relates to a kit comprising a recipient containing the lyophilized extract, a recipient containing a reconstitution solution or carrier and instructions for use.

The fibrin sealant components can be prepared from blood compositions. The blood composition can be whole blood or blood fractions, i.e. a product of whole blood such as plasma.

In one embodiment of the invention, the fibrinogen component is comprised from a biologically active component (BAC) which is a solution of proteins derived from blood plasma which can further comprise tranexamic acid and arginine or lysine or mixtures or arginine and lysine, or their pharmaceutically acceptable salts. BAC can be derived from cryoprecipitate, in particular concentrated cryoprecipitate.

The composition of BAC can comprise stabilizers such as arginine hydrochloride. Typically, the amount of fibrinogen in BAC is in the range of from about 40 to about 60 mg/ml. The amount of tranexamic acid in the solution of BAC can be from about 80 to about 110 mg/ml. The amount of arginine hydrochloride can be from about 15 to about 25 mg/ml.

Optionally, the solution is buffered to a physiological compatible pH value. The buffer can be composed of glycine, sodium citrate, sodium chloride, calcium chloride and water for injection as a vehicle. Glycine can be present in the composition in the amount of from about 6 to about 10 mg/ml, the sodium citrate can be in the range of from about 1 to about 5 mg/ml, sodium chloride can be in the range of from about 5 to about 9 mg/ml and calcium chloride can be in the concentration of about 0.1-0.2 mg/ml. Optionally, the BAC component can be diluted to comprise 3-60 mg/ml fibrinogen. The dilution can be carried out e.g. using a solution comprising glycine, sodium citrate, sodium chloride, calcium chloride and water for injection.

In one embodiment, the thrombin component used can be in a range of 100-1200 IU/ml.

During application of the liquid fibrin sealant formulation onto the desired location, the fibrinogen containing component and the thrombin containing component may be applied in any desired range of ratios. For example, when the concentration of the fibrinogen component is 3-60 mg/ml and the thrombin concentration is about 10-1200 IU/ml the two components can be mixed in a ratio of 1:1, 2:1, 3:1, 4:1, 5:1, 6:1, respectively, and so on. In one embodiment of the invention, the components of the liquid fibrin sealant are applied in a ratio of 3:1.

In another embodiment, the concentration of plasminogen and plasmin in the BAC composition is lowered to equal or less than 15 µg/ml like for example 5 µg/ml or less plasminogen e.g. using a method as described in U.S. Pat. No. 7,125,569 and WO02095019. In this case addition of tranexamic acid, aprotinin or any other fibrinolytic inhibitors into the BAC is not needed.

It is also possible that the fibrin sealant comprises components which encourage the formation of the clot, such as $Ca^{2+}$, Factor VIII, Factor XIII, fibronectin, vitronectin, von Willebrand factor (vWF) which can be provided as a separate component or formulated with the fibrin sealant components.

Fibrin sealant components derived from blood compositions are typically purified from infective particles. The purification procedure can be carried out by nanofiltration; solvent/detergent treatment and/or by any other method known in the art.

The term "infective particle" refers to a microscopic particle, such as micro-organism or a prion, which can infect or propagate in cells of a biological organism. The infective particles can be viral particles.

The platelet extract prepared according to the invention can be used in combination with various cell types e.g. fibroblast and stem cells e.g. endothelial stem cells e.g. HUVEC. The cell type can be determined according to the intended therapeutic use. For example, for regeneration of intervertebral disc, a cell composition comprising notochordal-derived cells can be used. For induction of angiogenesis, endothelial stem cells can be used.

The following examples are illustrative but not limiting.

EXAMPLES

Materials and Methods

Washed aphaeresis platelets leukocyte-reduced (WAP) preparation.

Platelet material units (platelets aphaeresis leukocyte-reduced units) were collected and processed according to the "Circular of Information for the Use of Human Blood and Blood Components" (December 2009) and conformed to applicable federal statuses and regulations of the FDA and US Department of Health. Each unit had a volume of approximately 200 ml. Each unit was drawn from a single donor who was screened and found acceptable for donation of a transfusable blood component based on FDA regulations, requirements and guidelines. Included were only units which were found non-reactive for red blood cell antibodies and negative for the following viruses by using FDA-approved kits and methods: Hepatitis B virus surface antigen; Antibody to hepatitis B virus core antigen; Hepatitis C virus antibody; Human T-cell lymphotrophic virus type 1 and 2 antibody; Human immunodeficiency virus types 1 and 2 antibody; HIV-1 by nucleic acid technology testing (NAT); HCV RNA by NAT; West Nile Virus RNA by NAT; and Serological test for syphilis. The minimal number of platelets in an aphaeresis leukocyte-reduced collected unit was as specified in the Circular of Information: $\geq 3.0 \times 10^{11}$ (the number of platelets in a single whole blood unit is $\geq 5.5 \times 10^{10}$).

All units were maintained under the recommended conditions for transfusion (see the direction for use for the blood collection, processing, and storage system approved by the FDA) until the washing step.

Washing Procedure.

Each unit was washed under aseptic conditions as follows:
1. Each unit was centrifuged at 4658×g for 6 minutes (rotor break was not used) at room temperature. Under these gentle conditions breakage of the cells was avoided.
2. The supernatant was discarded and the platelet pellet was re-constituted in 200 ml sterile docked saline (a way of transferring liquids between containers in a closed system to maintain aseptic conditions).
3. A second centrifugation was carried out in the same conditions specified in step 1.

4. The saline was discarded and the pelleted platelets were re-suspended in 200 ml sterile docked saline.
5. The washed and re-suspended platelets were frozen at −20 to −30° C. The freezing step was carried out within 4 hours from the previous step.

The above elaborated collection and washing procedures of the leukocyte-reduced platelets aphaeresis unit were carried out in a blood collection center (Rock River Valley Blood Center, Rockford, Ill./FDA License #249). The final WAP bags were supplied for the experiments within two months from the date of preparation. The units were received frozen on dry ice.

Prior to further processing the individuals frozen units (bags) were thawed and then pooled together or pooled while frozen and thawed together. The thawing procedure was carried out at 25° C. while stirring at 30 RPM using a stainless steel propeller connected to a RK1 overhead stirrer (Heidolph Instruments, Germany).

Growth Factors Recovery.

The concentrations of several growth factors in the samples were detected and measured using specific commercial ELISA kits (Quantikine by R&D Systems, MN USA: Human TGF-β1 Cat. DB100B, Human FGF basic Cat. HSFB00D, Human VEGF Cat. DVE00. Human PDGF-AB Cat. DHD00B. Human PDGF-BB Cat. DBB00, and Human EGF Cat. DEG00). In all the experiments below, growth factors content was measured in the lysate before loading the sample to the chromatography resin (pre-SDR material) and after collecting the sample from the resin (following solvent and detergent removal; post-SDR material), and the percentage of recovery of the growth factor following S/D removal was calculated.

Cell Count.

3T3-Swiss Albino fibroblasts cells (ATCC, Cat. number CCL92) were grown as an adherent monolayer. Every 2-3 days, the flasks were examined for confluence using a microscope.

The counting procedure was carried out as following:
The culture medium was aspirated.
The cell layer was briefly rinsed with 10 ml PBS to remove all traces of serum.
5 ml of Trypsin-EDTA (0.05% and 0.02%, respectively) solution were added per 175 cm2 flask and the cells were observed under an inverted microscope until the cell layer was dislodged from the plate surface (usually within 3 to 5 minutes).
10 ml of complete growth medium [DMEM; Biological Industries, Israel; Cat. number 01-055-1A containing 4.5 gr/l glucose and supplemented with 4 mM glutamine (Biological Industries, Israel; Cat. number 03-020-1B), 10% fetal calf serum (FCS; HyClone. USA; Cat. number SH30070.03), penicillin (100 U/ml)/streptomycin (0.1 mg/ml)/amphotericine (0.25 μg/ml) solution (P/S/A; Biological Industries. Israel; Cat. number 03-033-1B)] were added, and the floating cell clumps/clusters were dispersed by gently pipetting up and down several times until a homogenous cell suspension was obtained.
The cell suspension was transferred into a 50 ml tube and centrifuged in a swinging bucket rotor at 1000×g. for 4 minutes at room temperature.
The supernatant (containing the medium) was discarded and the pellet (containing the cells) was re-suspended in 3-10 ml of fresh complete growth medium as above.
10 μl of the cell suspension were loaded in the haemocytometer for cell counting.

Proliferation Assay.
On Day 1:
The cells were counted (as elaborated above), diluted to a concentration of 25,000 cells/ml with complete growth medium (GM) and 100 μl from the cell solution were seeded and allow to adhere in rows B-G of a 96-well plate (a final cell concentration of 2500 cells per well). Rows A+H were left empty. The plates were incubated for 24 hours at 37° C. in a water-jacketed incubator with 5% $CO_2$.

On Day 2:
The growth medium was aspirated and the plate adhered cells were washed twice with starvation medium [DMEM containing 4.5 gr/l glucose supplemented with 4 mM glutamine, 1% MEM-EAGLE non-essential amino acids (Biological Industries, Israel; Cat. number 01-340-1B, 1% human serum albumin (Plasbumin 25, Talecris Biotherapeutics, Germany) and P/S/A (in the concentrations listed above)](SM) (about 100 μl/well each wash) and fresh 100 ul/well SM were added to all wells (rows A-H). The plates were incubated for 24 hours at 37° C. in a water-jacketed incubator with 5% $CO_2$.

On Day 3:
10 μl of undiluted or serially diluted tested material/extract (prepared according to a given treatment) was added to a well (in three replicates) and incubated for additional 48 hours at 37° C. in a water-jacketed incubator with 5% $CO_2$. Diluted samples were prepared by performing 6 or 9 serial dilutions of 1:2 or 1:3 with starvation medium.

On Day 4:
10 μl of a cell proliferation measuring reagent WST-1 (Roche Diagnostics, Mannheim. Germany; Cat. number 11-644-807; this reagent is designed to be used for the non-radioactive, spectrophotometric quantification of cell proliferation, growth, viability and chemosensitivity in cell populations using a 96-well-plate format) were added to each well. After an additional incubation of 4 hours at 37° C. in a water-jacketed incubator with 5% $CO_2$, the 96-well plate was read at 450 nm and 650 nm in an ELISA reader after blanking the instrument on the blank wells (rows A+H), containing the medium only.

Evaluation of Results.

The results obtained by ELISA reader at 650 nm were subtracted from the results obtained at 450 nm per each well separately. The values were further analyzed by Prism software (GraphPad Software, Inc). To reduce the background reading, the results obtained for the untreated wells (containing cell that were not treated with the test materials) were subtracted from all the values of wells on the same 96-wells plate. The obtained results were used to plot a sigmoidal dose response curve against the log of the material concentration. In addition, $R^2$ fit, median effective concentration (EC50), and 95% Confidence Intervals EC50 values were calculated by GraphPad Prism software.

Thrombin Activity.

Thrombin activity was assessed by clotting time measurements using STart4 Coagulation Instrument (Diagnostica Stago, Asnières sur Seine, France). The assay is a modification of the European Pharmacopoeia Assay procedure, 1997, 0903, p. 858. Briefly, a calibration curve was prepared by mixing thrombin standard with a fibrinogen solution of 0.1% fibrinogen content (Enzyme Research Laboratories, IN, USA). Thrombin concentration in the different tested extract samples is then calculated from the calibration curve by their clotting time (the concentration is interpolated from the calibration curve). Prior to the measurements the tested extract samples were mixed 1:1 (w/w) with thrombin 16 IU/ml (Omrix, Israel) to reach a final concentration of 8 IU thrombin/ml. For the calibration curve, a 8 IU thrombin/ml standard sample was prepared by mixing the same 16 IU thrombin/ml solution 1:1 (w/w) with thrombin dilution buffer (0.4% tri-sodium citrate di-hydrate, 0.9% sodium chloride and 1% BSA, pH=7.5). A positive control sample for the treatment was made by mixing the same 16 IU thrombin i/ml solution 1:1 (w/w) with a platelet extract sample which was not S/D treated and did not contain heparin, LMWH or PVP (prepared as in Example 1). Thrombin activity was measured in each lysate prior to and after the column. The results are shown relative to the control sample (considered as 100% thrombin activity).

PVPs used in the experiments below.

In Table 30 below the concentration w/w of different PVPs and their corresponding concentration in mM are shown.

PVP is characterized by its K-value, or the Fikentscher's viscosity coefficient, which is a function of the average molecular weight, the degree of polymerization, and the intrinsic viscosity. The average molecular weight of the soluble Kollidon grades is expressed in terms of the K-value in the pharmacopoeias valid in Europe and the USA.

PVP polymer is made by a polymerization reaction in which monomers are joined together. Different molecular weights of PVP are made by controlling the termination of the polymerization reaction. This gives rise to the different types of PVPs, each with its own range of MW. There are several methods to determine the MW of PVP. Of note, the K-value and viscosity are not interchangeable. K-value is calculated from the viscosity in water.

In all the experiments below the listed percentages of PVP are w/w or mM. Also, the acetate/glycine/HSA percentages are calculated as w/w.

In all platelet lysate preparations below, the osmolarity of the pooled WAP was about 260-280 mOs [measured by using The Advanced™ Micro Osmometer Model 3300 (Advanced Instruments Inc, Norwood, Mass., USA)]. In order to keep the osmolarity level as constant as possible throughout the process, buffer osmolarity was monitored and adjusted, if needed, to that of the WAP starting material using NaCl (Sigma-Aldrich, St. Louis, Mo., USA).

Example 1: Platelet Extract Prepared from Pooled Washed Aphaeresis Platelets Leukocyte Reduced (WAP), Treated with S/D, Admixed with Heparin, and Subjected to S/D Removal In the following example the effect of including non-fractionated heparin [Heparin Sodium-Fresenius 5000 i.u./1 ml (injection) Bodene (PTY) Limited. South Africa] during S/D removal by hydrophobic interaction chromatography (HIC) on the recovery of TGF-β1, PDGF-AB, PDGF-BB, bFGF, VEGF, and EGF was examined. Heparin was tested since it is known to bind some growth factors. Heparin has a wide range of molecular weight, and by non-fractionated heparin it is meant that there was no isolation or selection of specific narrower range of molecular size.

S/D removal was carried out using SDR HyperD solvent-detergent removal chromatography resin (Pall Corp). SDR HyperD is a chromatographic packing made of silica beads in which the pore volume is filled with a three-dimensional cross-linked hydrophobic acrylic polymer. The SDR HyperD involves a mixed-mode adsorption of hydrophobic interaction and is associated with a molecular exclusion effect [Guerrier L et al. "Specific sorbent to remove solvent-detergent mixtures from virus-inactivated biological fluids". J Chromatogr B Biomed Appl. 1995 Feb. 3; 664(1):119-125].

2 ml of the resin were packed in a 1 cm diameter Bio-Rad column (small scale experiment). The S/D treated platelet lysate samples were prepared using 965-2328 g pooled washed apheresis platelets leukocyte reduced (WAP) obtained from 5-12 bags (each bag is obtained from one donor). 20 mM sodium acetate, 10 mM glycine and 0.2% human serum albumin (HSA) W/W (from the final volume solution) were added into the pooled WAP. In the next step, 1% Triton X-100 and 0.3% TnBP were added into the solution, and the solution was incubated and mixed (on a tube roller) at room temperature (22±2° C.) for 2 hours for platelet lysis and antivirus treatment. The stock lysate was then aliquoted (14 ml) into vials, frozen and stored at −80° C. until use. Prior to use, the aliquoted lysate was thawed in a 37° C. water bath, filtered through 5 μm syringe filter to remove any particulate matter and mixed on a roller mixer for at least 5 minutes.

The packed columns with the resin were washed, prior to loading the S/D treated lysate, with 10 ml Purified Water, and equilibrated with 10 ml acetate-glycine-HSA buffer pH 6.8-7.4 (abbreviated as "AGA"; concentration as above; In the experiments below all AGA used was at a pH of 6.8-7.4) with or without heparin according to the lysate's buffer (AGA with or without heparin). In the next step, 10 ml of the S/D-treated lysate were loaded onto the column except for samples 2 and 4 which were incubated with 5 IU heparin/ml (50 μl heparin was added into 50 ml of platelet lysate) prior to loading the lysate onto the column. The flow rate was kept up to 0.4 ml/min. Prior to loading the column, all samples with or without heparin, were mixed on a tube roller for 20 minutes at room temperature (22±2° C.). The residual S/D-treated lysate material (which was not loaded onto the column) was transferred into 1.5 ml vials and kept at −80° C. for analysis for growth factor concentration measurements and was regarded as loading control/pre-SDR material.

After loading the lysates, the columns were loaded with different buffers (as shown in the Table 1 below), 10 ml each. Each buffer contained different ingredients at different concentrations. In some of the buffers, heparin was combined with NaCl/ethanol. The flow rate was kept at or below 0.8 ml/min. All fractions obtained from the column after loading, and after washing with the buffers were collected, combined, and the collected material was divided into 1 ml aliquots and was kept frozen under −80° C. until proceeding with the measurements of growth factor recovery. This material was regarded as post-SDR removal material.

The recovery of different growth factors (% relative to the pre-SDR material) is shown in Table 2.

TABLE 1

A detailed description of samples and conditions used during the S/D removal step.

| Treatment | Sample loaded | Buffer 1 | Buffer 2 | Buffer 3 | Final volume of post-SDR material (ml) |
|---|---|---|---|---|---|
| 1 | S/D treated Lysate | AGA | AGA + 12.5% EtOH + 0.5M NaCl + 5 IU/ml heparin | AGA + 10% EtOH + 1M NaCl | 40 |

TABLE 1-continued

A detailed description of samples and conditions used during the S/D removal step.

| Treatment | Sample loaded | Buffer 1 | Buffer 2 | Buffer 3 | Final volume of post-SDR material (ml) |
|---|---|---|---|---|---|
| 2 | S/D treated Lysate + 5 IU/ml Heparin | AGA | AGA + 12.5% EtOH + 0.5M NaCl + 5 IU/ml heparin | AGA + 10% EtOH + 1M NaCl | 40 |
| 3 | S/D treated Lysate | AGA + 12.5% EtOH + 0.5M NaCl + 5 IU/ml heparin | AGA + 10% EtOH + 1M NaCl | | 30 |
| 4 | S/D treated Lysate + 5 IU/ml Heparin | AGA + 12.5% EtOH + 0.5M NaCl + 5 IU/ml heparin | AGA + 10% EtOH + 1M NaCl | | 30 |

TABLE 2

Recovery of various growth factors in a platelet extract following S/D removal step (% relative to pre-SDR column) according to the samples and conditions in Table 1.

| | Growth factor Recovery (%) | | | | | |
|---|---|---|---|---|---|---|
| Treatment | PDGF-AB | PDGF-BB | bFGF | VEGF | EGF | TGF-β1 |
| 1 | 50.4 | 62.6 | 52.6 | 55.8 | 54.9 | 76.1 |
| 2 | 49.1 | 77.3 | 92.9 | 62.4 | 50.3 | 77.3 |
| 3 | 61.7 | 86.0 | 53.7 | 66.7 | 66.9 | 76.2 |
| 4 | 60.6 | 92.1 | 97.0 | 50.2 | 56.7 | 66.9 |

The results presented in Table 2 show that incubation of an S/D-treated platelet lysate with heparin prior to loading the material to an SDR column (treatments 2 and 4 vs. 1 and 3) resulted in a dramatic increase in the recovery of bFGF from about 53% to about 93 or 97%. The recovery of PDGF-BB also increased, but to a lesser extent. Treatments 2 and 4, which included a combination of incubation with heparin prior to loading to the SDR column and an additional washing step with heparin resulted in a significant enrichment of the resulting platelet extract with PDGF-AB and PDGF-BB which is further increased in treatment 4 (61% and 92% recovery, respectively) by washing the column, immediately after loading, with a buffer containing heparin as opposed to treatment 2 in which preceding the use of the heparin containing buffer, the column is washed with a buffer without heparin.

Therefore, the results show that contacting the S/D treated platelet lysate with heparin prior to the removal of the S/D, e.g. by HIC, can advantageously increase the recovery of certain growth factors. e.g. bFGF and PDGF-BB.

Figure 1:
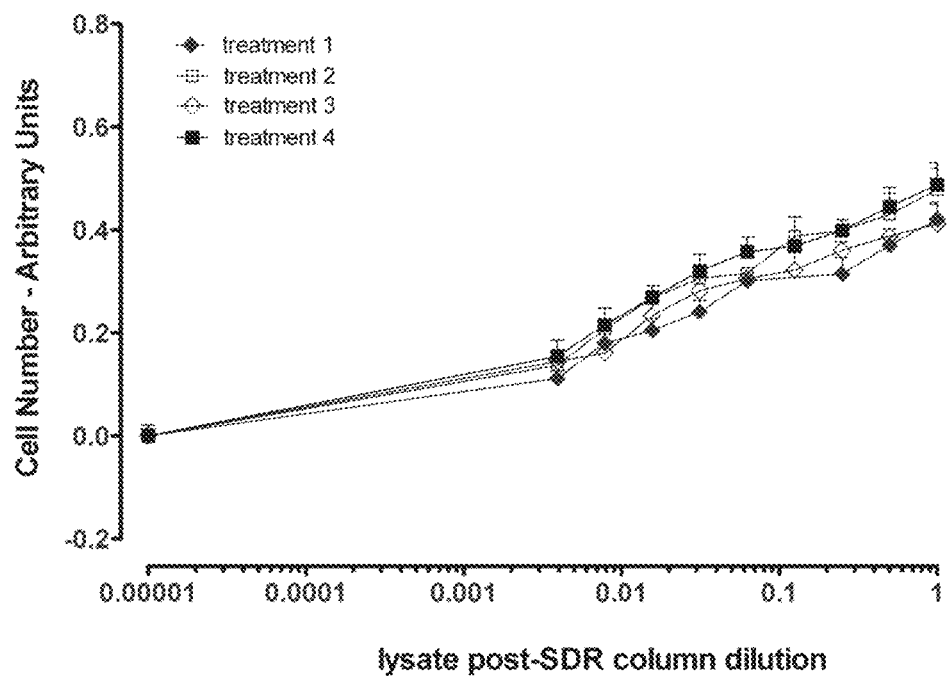
FIG. 1 shows proliferation of 3T3 fibroblast cells treated with a platelet extract obtained by contacting the lysate with heparin prior to S/D removal (treatment 2 and 4). A platelet extract prepared without contacting the lysate with heparin prior to S/D removal served as the control (treatment 1 and 3).

Example 2: The Effect of Platelet Extract Prepared by Admixing the Lysate with Heparin Prior to S/D Removal on Fibroblast Cell Proliferation In the following example the biological effect of a platelet extract prepared by contacting the lysate with heparin prior to S/D removal on 3T3-Swiss Albino fibroblast cell proliferation was examined. Four extracts prepared according to the different four steps elaborated in Table 1 were examined. The results are shown in FIG. 1.

The cell proliferation results (FIG. 1) show that samples obtained by treatments 2 and 4 including incubation with heparin prior to loading on the SDR column were significantly more effective in inducing proliferation than samples obtained by treatments 1 and 3 that were not incubated with heparin. Samples obtained by treatment 2 and 4 had EC50 of 0.99 and 0.89, respectively, whereas samples obtained by treatments 1 and 3 had EC50 of 2.93 and 2.4, respectively.

These results demonstrate that incubation with heparin prior to S/D removal, which resulted in higher GFs recovery, also improved biological potency as reflected by the fibroblasts proliferation assay.

Example 3: The Effect of Admixing an S/D-Treated Lysate with Low Molecular Weight Heparin Prior to S/D Removal Step Low molecular weight heparins (LMWHs) are heparins having an average molecular weight of about 4.5 kDa compared to 15 kDa of an unfractionated heparin. In the clinical setting, LMWH has several pharmacological and practical advantages over unfractionated heparin. LMWH have been shown to have less unspecific binding to cells and proteins, has a longer plasma half-life, and can therefore be administered subcutaneously (Hirsh and Raschke, Heparin and low-molecular-weight heparin: the Seventh ACCP Conference on Antithrombotic and Thrombolytic Therapy. Chest. 2004; 126:188S-203S).

In the following example the effect of different conditions used during the HIC S/D removal step on the recovery of PDGF-AB, PDGF-BB, bFGF, VEGF, and EGF were examined (see the different conditions in Table 3). In this experiment, Enoxaparin sodium (Clexane, Sanofi Aventis) was used as a low molecular weight heparin.

The lysates were prepared and then loaded to an SDR column as elaborated in the experiment above under the conditions elaborated in Table 3. Prior to loading, equilibration was carried out using the buffer of the loaded lysate. All fractions obtained from the column after loading, and after washing with the buffers were collected, combined, and the total growth factors recovery was calculated. Treatment 2 included incubation with 5 IU/ml Enoxaparin in the same manner as was carried out for heparin above. The results are shown in Table 4.

TABLE 3

A detailed description of samples and conditions used during the S/D removal step.

| Treatment | Sample loaded | Buffer 1 | Buffer 2 | Buffer 3 | Final volume of post-SDR material |
|---|---|---|---|---|---|
| 1 | S/D treated lysate | AGA | AGA + 12.5% EtOH + 0.5M NaCl + 5 IU/ml Enoxaparin | AGA + 10% EtOH + 1M NaCl | 40 |

TABLE 3-continued

A detailed description of samples and conditions used during the S/D removal step.

| Treatment | Sample loaded | Buffer 1 | Buffer 2 | Buffer 3 | Final volume of post-SDR material |
|---|---|---|---|---|---|
| 2 | S/D treated lysate + 5 IU/ml Enoxaparin | AGA + 12.5% EtOH + 0.5M NaCl + 5 IU/ml Enoxaparin | AGA + 10% EtOH + 1M NaCl + 5 IU/ml Enoxaparin | | 30 |

TABLE 4

Recovery of various growth factors in a platelet extract following S/D removal step (% relative to pre-SDR column) according to the samples and conditions in Table 3.

| | Growth factor Recovery (%) | | | | |
|---|---|---|---|---|---|
| Treatment | PDGF-AB | PDGF-BB | bFGF | VEGF | EGF |
| 1 | 38.8 | 63.9 | 43.0 | 53.4 | 63.7 |
| 2 | 55.9 | 74.9 | 61.5 | 58.2 | 60.4 |

The results presented in Table 4 show that incubation of the S/D-treated platelet lysate with Enoxaparin prior to S/D removal step (treatment 2 vs. 1), and an additional Enoxaparin-containing washing step increased the recovery of PDGF-AB, PDGF-BB and bFGF.

However, the recoveries following contact with 5 IU/ml unfractionated heparin (treatment 4 in Table 1; Example 1 above) for PDGF-BB and bFGF (92% and 97%, respectively) were higher than with 5 IU/ml Enoxaparin (75% and 62%, respectively). An additional experiment with increased Enoxaparin concentration (30 IU/ml; data not shown), did not result in any significant change in growth factor recoveries.

Figure 2:
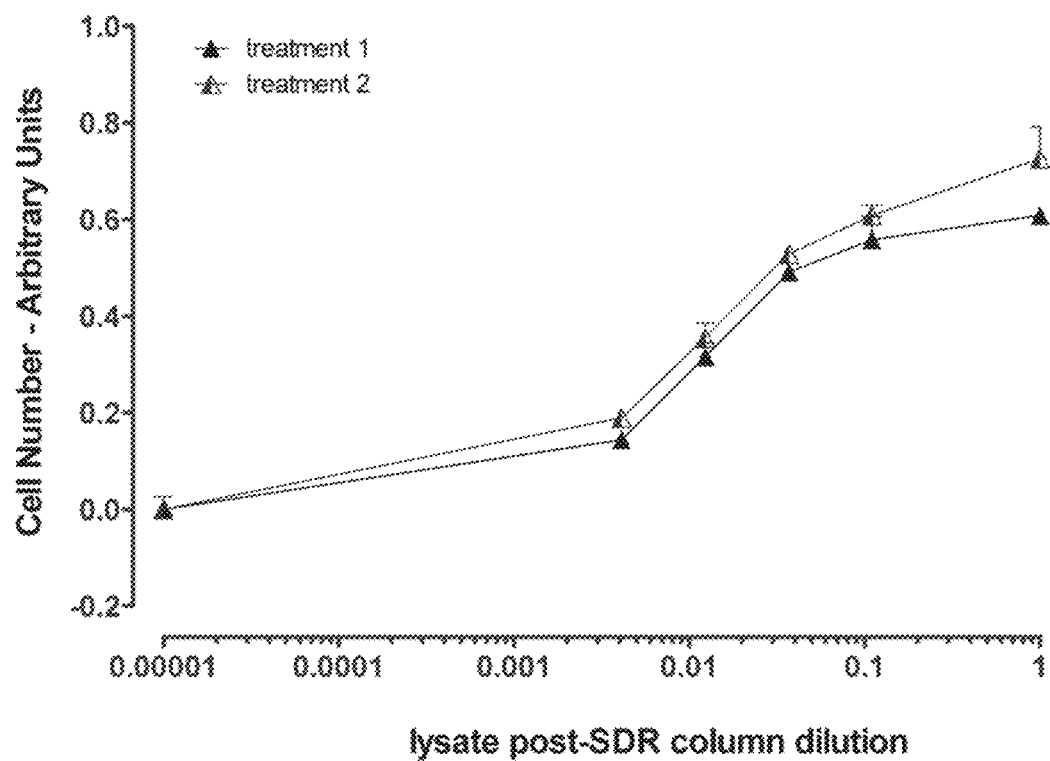
FIG. 2 shows proliferation of 3T3 fibroblast cells treated with a platelet extract prepared by contacting the lysate with low molecular weight heparin (LMWH) prior to and during S/D removal (treatment 2). A platelet extract obtained following S/D removal in the absence of contacting the lysate with low molecular weight heparin (LMWH) prior to S/D removal served as the control (treatment 1).

Example 4: The Effect of Platelet Extract Prepared by Admixing the Lysate with Low Molecular Weight Heparin Prior to S/D Removal on Fibroblast Cell Proliferation In the following example the effect of a platelet extract prepared as described in Example 3 on cell proliferation was examined. Cell count and proliferation assay was carried out as elaborated in the "MATERIALS and METHODS" section using 3T3-Swiss albino fibroblast cells. The results are shown in FIG. 2.

The results (FIG. 2) show that fibroblasts proliferation was higher in the sample that was incubated with LMWH (sample 2/treatment 2, EC50 0.05) compared with the sample that was not incubated with LMWH (sample 1/treatment 1, EC50 0.11).

These results demonstrate that incubation with low molecular weight heparin prior to S/D removal increases the recovery of some growth factors (Example 3) and also improves the biological potency.

Example 5: The Effect of Admixing a Platelet Lysate with PVP Prior to S/D Removal on Growth Factor Recovery In the previous Example, prior to S/D removal, the lysate was contacted with unfractionated heparin and LMWH, which are known to bind certain growth factors.

In the following Example, PVP, a completely different compound having amphiphilic characteristics, was explored on its effect on growth factor recovery following S/D removal by HIC column.

In this example different S/D removal conditions were tested with or without (control) the addition of PVP prior to or during the HIC S/D removal step. The recovery of the following growth factors was examined: TGF-β1, PDGF-AB, PDGF-BB, bFGF, VEGF, and EGF using the commercial ELISA kits listed above. Two types of PVP were tested: K25 (Kollidon® 25 having a K-Value of 22.5-27.0 and an average molecular weight of 30000 Da, Cat. 02286 Sigma Life Sciences, Germany); and K30 (Povidone K-30 having a K-Value of 27.0-32.4 and an average molecular weight of 40000 Da, Cat. P1454 Spectrum chemical mfg corp. USA).

The lysates were prepared and loaded onto a SDR column as elaborated in Example 1 above and by using the S/D removal conditions as elaborated in Table 5. Prior to loading, equilibration was carried out using the buffer of the loaded lysate. All fractions obtained from the column after loading, and after washing with buffer 1 and buffer 2 were collected, combined, and the growth factor recovery was calculated. Growth factor recovery results (calculated as explained above) are shown in Table 6. All loaded samples that comprised PVP were also incubated with PVP in the manner discussed above.

TABLE 5

A detailed description of samples and conditions used during the S/D removal step.

| Treatment | Sample loaded | Buffer 1 | Buffer 2 |
|---|---|---|---|
| 7 | S/D treated lysate + 1% (0.25 mM) PVP 30 | AGA + 0.1% (0.025 mM) PVP 30 + 0.5M NaCl + 12.5% EtOH | AGA + 1% PVP 30 |
| 3 | S/D treated lysate + 1% (0.3 mM) PVP 25 | AGA + 0.1% (0.03 mM) PVP 25 + 0.5M NaCl + 12.5% EtOH | AGA + 1% PVP 25 |
| 6 | S/D treated lysate + 0.1% PVP 25 | AGA + 0.1% PVP 25 | AGA + 0.1% PVP 25 |
| 8 | S/D treated lysate + 0.1% PVP 30 | AGA + 0.1% PVP 30 + 0.5M NaCl + 12.5% EtOH | AGA + 0.1% PVP 30 + 1M NaCl + 12.5% EtOH |
| 9 | S/D treated lysate + 1% PVP 30 | AGA + 0.1% PVP 30 | AGA + 1% PVP 30 |
| 5 | S/D treated lysate + 1% PVP 25 | AGA + 0.1% PVP 25 | AGA + 1% PVP 25 |
| 2 | S/D treated lysate | AGA + 0.5M NaCl + 12.5% EtOH | AGA + 1M NaCl + 12.5% EtOH |

TABLE 5-continued

A detailed description of samples and conditions
used during the S/D removal step.

| Treatment | Sample loaded | Buffer 1 | Buffer 2 |
|---|---|---|---|
| 4 | S/D treated lysate + 0.1% PVP 25 | AGA + 0.1% PVP 25 + 0.5M NaCl + 12.5% EtOH | AGA + 0.1% PVP 25 + 1M NaCl + 12.5% EtOH |
| 10 | S/D treated lysate + 0.1% PVP 30 | AGA + 0.1% PVP 30 | AGA + 0.1% PVP 30 |
| 1 | S/D treated lysate | AGA + 0.5M NaCl + 12.5% EtOH | AGA |

TABLE 6

Recovery of various growth factors in a platelet extract
following S/D removal step (% relative to pre-SDR column)
according to the samples and conditions in Table 5.

| | Growth factor Recovery (%) | | | | |
|---|---|---|---|---|---|
| Treatment | PDGF-AB | PDGF-BB | bFGF | EGF | VEGF |
| 7 | 90 | 90 | 100 | 65 | 81 |
| 3 | 83 | 86 | 88 | 67 | 72 |
| 6 | 80 | 94 | 59 | 59 | 60 |
| 8 | 70 | 87 | 66 | 57 | 49 |
| 9 | 58 | 34 | 89 | 69 | 82 |
| 5 | 47 | 29 | 83 | 67 | 82 |
| 2 | 48 | 65 | 28 | 59 | 51 |
| 4 | 29 | 30 | 35 | 65 | 79 |
| 10 | 41 | 45 | 53 | 62 | 63 |
| 1 | 49 | 45 | 20 | 50 | 55 |

The results show that contacting an S/D-treated platelet lysate with PVP prior to and during S/D removal by an SDR column greatly affected the recovery of growth factors from an SDR column.

Also, the results show that, during the S/D removal step, PVP combined with ethanol and NaCl was more effective in increasing growth factor recovery than PVP alone (compare treatments 7 vs. 9, and 3 vs. 5).

The results also show that using a lower molecular weight PVP resulted in a further increase in growth factor recovery (compare treatment 3 with 7).

It can be concluded that an increase in growth factor recovery, when subjecting an S/D treated lysate to an S/D removal step, can be achieved by contacting the S/D treated lysate with PVP prior to and/or during the S/D removal step.

Example 6: The Effect of the Molecular Weight of the PVP Polymer Used Prior to and During S/D Removal on Fibroblast Cell Proliferation In the following example the effect of the molecular weight of the PVP contacted with an S/D treated lysate prior to and during S/D removal on cell proliferation was examined.

Platelet lysate samples prepared according to the S/D removal procedure elaborated for treatments 3 and 7 in Table 5 (Example 5) were used.

Cell count and cell proliferation assay were carried out as elaborated in the "MATERIALS and METHODS" section using 3T3-Swiss albino fibroblast cells.

Figure 3:
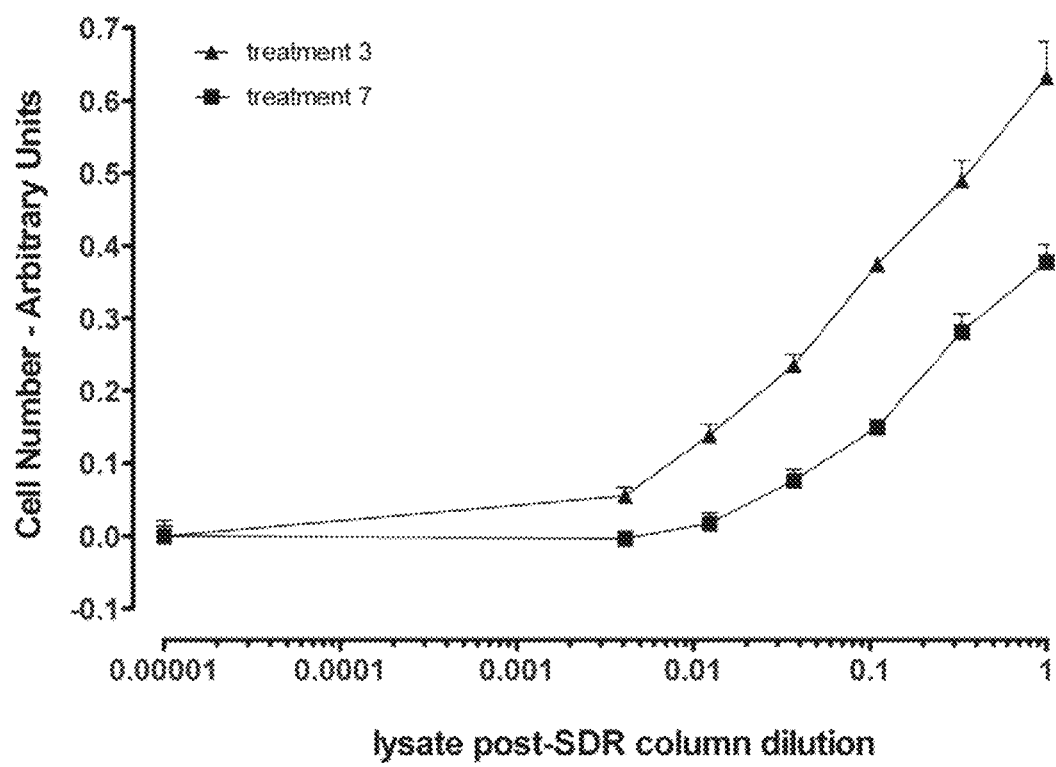
FIG. 3 shows proliferation of 3T3 fibroblast cells treated with extracts obtained after S/D removal in the presence of different molecular weight PVP polymers: PVP K25—treatment 3; or PVP K30—treatment 7.

The results are shown in FIG. 3.

The results show that sample 3 comprising PVP K25 had a higher proliferation rate (EC50=0.34) than sample 7 comprising PVP K30 (EC50=1.95). Although, as indicated in Example 5, the recovery of growth factors resulting from treatment 7 was higher than the recovery of growth factors resulting from treatment 3, the activity of the growth factors recovered in treatment 3 is much more effective than the activity of the growth factors recovered in treatment 7.

These results suggest that in order to obtain an increased biological potency, a lower molecular weight of PVP (e.g. PVP K25) can be advantageously used.

Example 7: The Effect of Different Concentrations of PVP Prior to and During S/D Removal on Growth Factor Recovery The following example aims to corroborate the previous results showing that using PVP, ethanol and/or NaCl during S/D removal step increases growth factor recovery from an SDR column. The effect of different conditions during the S/D removal step was examined and the recovery of several growth factors in the post-SDR material was measured as specified above (TGF-β1, PDGF-AB, PDGF-BB, bFGF, VEGF, and EGF).

PVP K25 (same as above) was used in these experiments. The lysates were prepared and loaded onto a SDR column as elaborated above in Example 1 using the S/D removal conditions as elaborated in Table 7 below. Prior to loading, equilibration was carried out with AGA (concentrations as above)+0.1% (0.03 mM) PVP K25. All samples contained a final concentration of 0.1% (0.03 mM) PVP K25 in AGA buffer (concentrations as above). All loaded samples were incubated with PVP in the manner discussed above before loading. All fractions obtained from the column after loading, and after washing with the buffers were collected, combined, and the growth factor recovery was calculated. The growth factor recovery results (% relative to the pre-SDR material) are presented in Table 8 and are listed from the highest to the lowest total growth factor recovery.

One aim was to try to reduce the PVP in the final product. In some experiments described in the preceding Examples, the sample was incubated with a relatively high PVP final concentration of 1% (Example 5). In some cases, after loading the column with the sample volume (6 column volumes) the column was washed with a relatively low PVP concentration of 0.1%. However, since the largest fraction by volume is the sample loaded (6 column volumes), the best way to reduce the PVP in the product is by reducing PVP concentration in the sample to be loaded e.g. by incubating the sample to be loaded with a final concentration of 0.1% (0.03 mM) PVP K25 instead of 1% (0.3 mM) PVP K25.

TABLE 7

A detailed description of samples and conditions
used during the S/D removal step.

| Treatment | Buffer 1 | Buffer 2 |
|---|---|---|
| 19 | AGA + 0.5% PVP | AGA + 0.5% PVP + 1M NaCl + 12.5% EtOH |
| 18 | AGA + 0.5% PVP + 0.5M NaCl + 12.5% EtOH | AGA + 0.1% PVP + 1M NaCl + 12.5% EtOH |

TABLE 7-continued

A detailed description of samples and conditions used during the S/D removal step.

| Treatment | Buffer 1 | Buffer 2 |
|---|---|---|
| 13 | AGA + 1% PVP | AGA + 0.1% PVP + 1M NaCl + 12.5% EtOH |
| 17 | AGA + 0.5% PVP | AGA + 0.1% PVP + 1M NaCl + 12.5% EtOH |
| 8 | AGA + 1% PVP + 1M NaCl + 12.5% EtOH | AGA |
| 7 | AGA | AGA + 1% PVP + 1M NaCl + 12.5% EtOH |
| 20 | AGA + 0.5% PVP + 0.5M NaCl + 12.5% EtOH | AGA + 0.5% PVP + 1M NaCl + 12.5% EtOH |
| 9 | AGA + 0.1% PVP | AGA + 1% PVP + 1M NaCl + 12.5% EtOH |
| 2 | AGA + 0.1% PVP | AGA + 0.1% PVP + 1M NaCl + 12.5% EtOH |
| 3 | AGA + 0.1% PVP + 0.5M NaCl + 12.5% EtOH | AGA + 0.1% PVP + 1M NaCl + 12.5% EtOH |
| 12 | AGA + 0.1% PVP + 1M NaCl + 12.5% EtOH | AGA + 1% PVP |
| 6 | AGA + 0.5M NaCl + 12.5% EtOH | AGA + 1% PVP + 1M NaCl + 12.5% EtOH |
| 11 | AGA + 0.1% PVP + 1M NaCl + 12.5% EtOH | AGA + 1% PVP + 1M NaCl + 12.5% EtOH |
| 10 | AGA + 0.1% PVP + 0.5M NaCl + 12.5% EtOH | AGA + 1% PVP + 1M NaCl + 12.5% EtOH |
| 14 | AGA + 0.5% PVP | AGA + 0.5% PVP |
| 16 | AGA + 0.5% PVP | AGA + 0.1% PVP |
| 4 | AGA | AGA + 1% PVP |
| 5 | AGA + 1% PVP | AGA |
| 15 | AGA + 0.1% PVP | AGA + 0.5% PVP |
| 1 | AGA + 0.1% PVP | AGA + 0.1% PVP |

TABLE 8

Recovery of various growth factors in a platelet extract following S/D removal step according to the samples and conditions in Table 7.

| Treatment | PDGF-AB | bFGF | VEGF | EGF | TGF-β1 |
|---|---|---|---|---|---|
| 19 | 76 | 73 | 75 | 60 | 74 |
| 18 | 89 | 74 | 50 | 57 | 83 |
| 13 | 75 | 56 | 49 | 64 | 101 |
| 17 | 71 | 65 | 72 | 63 | 70 |
| 8 | 74 | 71 | 71 | 55 | 65 |
| 7 | 72 | 60 | 67 | 57 | 74 |
| 20 | 73 | 56 | 50 | 54 | 88 |
| 9 | 61 | 68 | 64 | 61 | 67 |
| 2 | 56 | 60 | 73 | 60 | 65 |
| 3 | 62 | 60 | 53 | 54 | 83 |
| 12 | 60 | 48 | 51 | 57 | 93 |
| 6 | 65 | 61 | 53 | 54 | 74 |
| 11 | 64 | 58 | 53 | 53 | 75 |
| 10 | 54 | 69 | 50 | 57 | 73 |
| 14 | 25 | 32 | 87 | 54 | 98 |
| 16 | 18 | 40 | 77 | 60 | 98 |
| 4 | 21 | 29 | 76 | 65 | 90 |
| 5 | 19 | 32 | 72 | 64 | 88 |
| 15 | 13 | 26 | 71 | 60 | 98 |
| 1 | 15 | 25 | 69 | 59 | 86 |

*% relative to pre-SDR column.

The results confirm the previous results and show that the highest growth factor recovery from the SDR column was obtained when the lysate was contacted with PVP in combination with ethanol and NaCl than when contacted with PVP alone during the S/D removal step.

The results also show that it is possible to reduce the PVP concentration in the product to below 0.5% (0.17 mM).

Example 8: The Effect of Different Concentrations of PVP in a Platelet Extract on Fibroblast Cell Proliferation The proliferative effect of samples prepared in Example 7 on cell proliferation was examined in the manner described in the "MATERIALS and METHODS" section using 3T3-Swiss albino fibroblasts cells.

In this experiment, cell proliferation activities of sample 17 and 19, which showed comparable amounts of growth factor recovery, were examined. The main difference between the two samples was that sample 17 was prepared by a second washing buffer comprising 0.1% (0.03 mM) PVP whereas sample 19 was prepared with a second washing buffer comprising 0.5% (0.17 mM) PVP (see Table 7). This difference resulted in two extract products having different PVP concentration.

The results show that cell proliferation activity in sample 17 which comprises a low PVP concentration (prepared with 0.1% PVP; EC50=2.3) was similar to that of sample 19 (prepared with 0.5% PVP; EC50 2.87) which comprises a higher PVP concentration.

Figure 4:
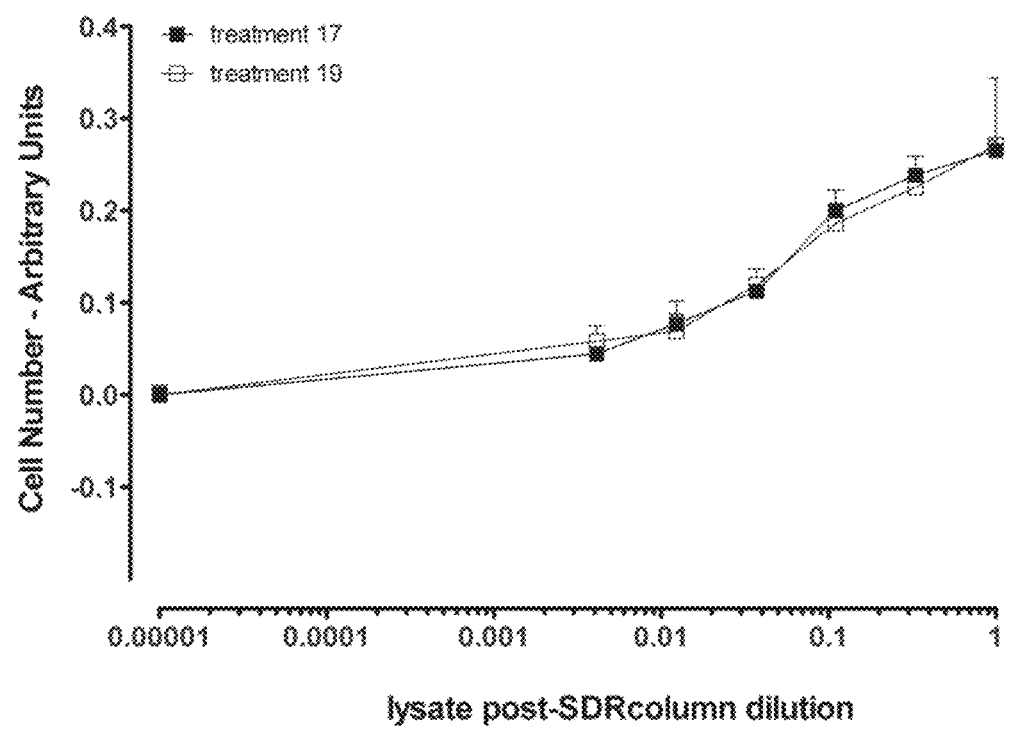
FIG. 4 shows proliferation of 3T3 fibroblast cells treated with extracts comprising different concentrations of PVP. Sample 17 (treatment 17) and sample 19 (treatment 19) differ in the second wash of the S/D removal, where 0.1% and 0.5% PVP were used, respectively.

The results (FIG. 4) show that higher amount of PVP in the product did not affect proliferation level.

Example 9: The Effect of PVP on Thrombin Activity

The following example was aimed to examine whether a platelet extract prepared using PVP or heparin during S/D removal affects thrombin activity.

Thrombin is a key enzyme of coagulation and is activated as the first step of the coagulation cascade. Thrombin acts as a serine protease that converts soluble fibrinogen into insoluble strands of fibrin, as well as catalyzes many other coagulation-related reactions.

The effect of heparin and LMWH on blood coagulation has been known and it is used principally in medicine for anticoagulation [Machovich R et al. "Effect of Heparin on Thrombin Inactivation by Antithrombin-III". Biochem. J. 1978; 173:869-875].

Thrombin activity was assessed by the clotting time measurement as described above. The results shown in Table 9 are relative to the control sample (which is considered as 100% thrombin activity).

TABLE 9

Thrombin activity (% relative to control sample) of platelet extract samples comprising heparin, LMWH or PVP 25.

| Heparin-comprising platelet extract sample** | | | LMWH-comprising platelet extract sample*** | | PVP K25-comprising platelet extract sample**** | |
|---|---|---|---|---|---|---|
| pre-SDR material | post-SDR material | | pre-SDR material | post-SDR material | pre-SDR material | post-SDR material |
| | Treatment 2 | Treatment 4 | | Treatment 2 | | Treatment 17 |
| 62* | 52* | 61* | 96* | 86* | 100* | 100* |

*Thrombin activity (%) relative to control sample.
**Prepared according to treatment 2 and 4 in Example 1.
***Prepared according to treatment 2 in Example 3.
****Prepared according to treatment 17 in Example 7.

The results show that platelet extract samples comprising unfractionated heparin or LMWH had an inhibitory effect on thrombin activity in vitro, whereas no inhibitory effect was detected with platelet extract samples comprising PVP.

Example 10: Platelet Extract Prepared from Pooled Washed Aphaeresis Platelets Leukocyte Reduced (WAP), Treated with S/D, Incubated with PVP K25, and Washed from a SDR Column with PVP K25 Prepared in a Large Scale Process In this experiment, the effect of PVP addition prior S/D removal on the recovery of growth factor was evaluated in higher scale (in the above experiments a small scale process was carried out). In this experiment PVP K25 was used.

The lysate was prepared as follows: Platelet lysate samples were prepared using 2328 g pooled washed apheresis platelet leukocyte reduced (WAP) obtained from 12 bags. 255 ml acetate-glycine buffer to a final concentration of 20 mM sodium acetate, 10 mM glycine; at pH 6.8-7.4 and Human Serum Albumin (HSA; Talecris USA) to a final concentration of 0.2% W/W from the final volume solution were added into the pooled WAP. In the next step, S/D treatment was carried out by slowly adding 1% Triton X-100 and 0.3% TnBP (w/w) into the pooled sample while mixing at 30 RPM. In order to avoid sub-optimal viral inactivation due to the possible presence of particulate matter, the S/D treatment was split into two parts. First, the sample was continuously stirred for 30 minutes, centrifuged at 5016×g for 10 minutes at 23-27° C., and filtered through 0.45 µm filter (Sartopore 2, Sartorius Stedim Biotech S.A., Aubagne, France). In the second part, the filtered material was poured into a stainless steel pot immersed in a water bath adjusted to 25° C. and mixed at 30 RPM for additional 2 hours to continue the viral inactivation process in a clear solution. PVP K25 was added to the S/D-treated lysate to a final concentration of 0.1% (w/w) (0.03 mM) and incubated for 20 minutes at 25° C. while stirring at 30 RPM. The sample was filtered using 5 µm Sartopore PP2 filter to remove particulate matter.

Next, S/D removal was carried out using XK50 liquid chromatography column packed with 300 ml SDR HyperD solvent-detergent removal chromatography resin (Pall Corp) in conjunction with a peristaltic pump and a UA-6 UW/WIS detector+Type 11 recorder (ISCO, NE, USA). The column was equilibrated with 900 ml of Acetate-Glycine buffer containing 20 mM Na-acetate, 10 mM glycine, 0.1% (0.03 mM) PVP and 0.2% HSA, pH 6.8-7.4. 1800 ml of S/D- and PVP-treated platelet lysate (which contained 1620 ml of platelet material) were loaded onto the column followed by washing the column with 600 ml acetate glycine buffer (same concentrations as above) containing 0.5% (0.17 mM) PVP and 0.2% HSA. This was followed by washing with 1,200 ml of Acetate-Glycine buffer containing 12.5% ethanol, 1M NaCl, 0.1% (0.03 mM) PVP and 0.2% HSA. Next, the column was washed with 300 ml of purified water. The extract included all fractions combined and collected from the column after loading, and after washing with the buffers. Growth factor recovery in the extract was measured and calculated.

A total volume of 3600 ml was collected from the column. The collected material was filtered using consecutively 3 and 1.2 µm Sartopure PP2 filters and a 0.45 µm Sartopore 2 filter (Sartorius Stedim Biotech S.A., Aubagne, France).

PDGF-AB, PDGF-BB, VEGF, TGF-β1, bFGF and EGF recoveries were calculated as described above.

TABLE 10

Recovery of the various growth factors in a platelet extract following S/D removal step according to the above conditions in a large scale process.

| Growth factor | Recovery (%)* |
|---|---|
| TGF-β1 | 83 |
| PDGF-AB | 73 |
| PDGF-BB | 87 |
| EGF | 59 |
| bFGF | 61 |
| VEGF | 76 |

*% relative to pre-SDR column.

The results presented in Table 10 show that the relatively high growth factor recoveries from the SDR column when using low concentration of PVP in combination with ethanol and NaCl are maintained when carrying out a large process scale. The concentration of PVP in the post-SDR extract was 0.17% (0.057 mM).

Figure 5:
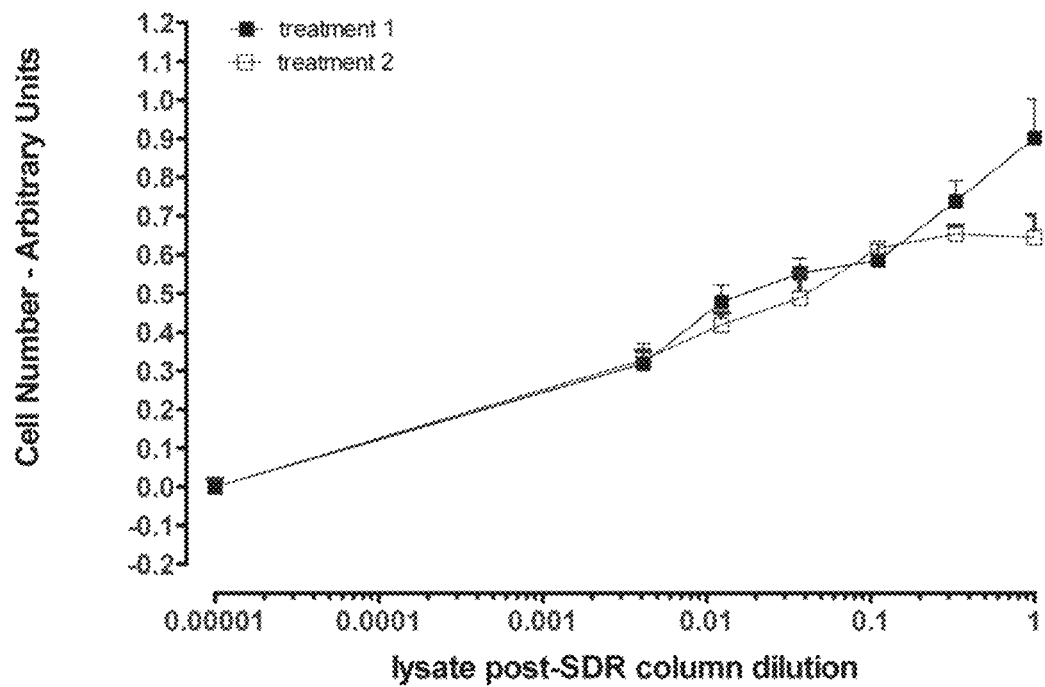
FIG. 5 shows proliferation of 3T3 fibroblast cells treated with large scale platelet extracts obtained after S/D removal in the presence of PVP K25 (treatment 1) or after S/D removal in the presence of heparin (treatment 2).

Example 11: The Effect of a Platelet Extract Prepared in a Large Scale Process by Contacting the Lysate with Low Concentration of PVP K25 Prior to and During S/D Removal on Fibroblast Cell Proliferation The effect of a sample prepared in the previous Example with PVP K25 on cell proliferation was carried out as elaborated above using 3T3-Swiss albino fibroblasts cells. The activity of the sample (marked as treatment 1 in FIG. 5)

was compared to the activity of a lysate prepared by contact with heparin as elaborated in Example 1 (marked as treatment 2 in FIG. 5).

The proliferation results are shown in FIG. 5.

The results show that platelet extract samples prepared in a large scale process had a positive proliferative effect (EC50=0.024) which is higher than the proliferative effect of a platelet extract sample prepared with heparin (EC50=0.047).

These results demonstrate that a platelet extract collected from a large scale SDR column as disclosed has a high growth factor recovery and thus has a biological activity when carried out in a large process scale.

Example 12: The Effect of Using PVP Prior to and/or During S/D Material Removal on the Residual Levels of S/D Material in the Post-SDR Material In the previous set of experiments it was shown that increased growth factor recovery was obtained while contacting the platelet lysate with PVP, ethanol and/or NaCl prior to and/or during the S/D removal step.

It is important to verify that PVP does not reduce the S/D binding capacity of the SDR resin, to ensure efficient S/D removal from the lysate.

In the following set of experiments, the efficacy of S/D (TritonX-100 and TnBP) removal under the same conditions as elaborated in Example 10 was evaluated.

Of note, the acceptable limit of both Triton X-100 and TnBP in blood-derived products is <5 ppm. The concentration of Triton X-100 and TnBP was measured prior (pre-SDR material) to and following (post-SDR material) the S/D removal step. Triton X-100 was determined by reversed phase HPLC with a U.V. detector, and TnBP was determined by capillary gas chromatography using a Flame Ionization Detector.

The results are shown in Table 11 below.

TABLE 11

S/D concentration in the lysate prior to and following S/D removal according to the conditions elaborated in Example 10.

| Material | S/D | ppm |
|---|---|---|
| pre-SDR material | Triton X-100 | 9,136 |
|  | TnBP | 2,586 |
| post-SDR material | Triton X-100 | <5 |
|  | TnBP | <0.3 |

In the above experiment, incubation/equilibration/washing were carried out in the presence of PVP K25 in a concentration of up to 0.5% (0.17 mM).

The results show that carrying out an S/D material removal in the presence of PVP K25 in a concentration of up to 0.5%, which was found to be efficient for growth factor recovery in the previous experiments, did not affect the S/D removal performance of the column.

Additional experiments (carried out in small scale process as shown in Example 5), wherein incubation/equilibration/washing were carried out in the presence of PVP K25 and K30 at a concentration of 1% (0.3 mM) resulted in the presence of Triton X-100 in the post-SDR. The results are shown in Table 12 below.

TABLE 12

S/D concentration in the lysate prior to and following S/D removal according to the conditions elaborated in Example 5.

| Treatment | Material | S/D | ppm |
|---|---|---|---|
| 3 | pre-SDR material | Triton X-100 | 8587 |
|  |  | TnBP | 2480 |
|  | post-SDR material | Triton X-100 | 60.8 |
|  |  | TnBP | <0.3 |
| 5 | pre-SDR material | Triton X-100 | 8587 |
|  |  | TnBP | 2480 |
|  | post-SDR material | Triton X-100 | 7.2 |
|  |  | TnBP | <0.3 |
| 7 | pre-SDR material | Triton X-100 | 8142 |
|  |  | TnBP | 2437 |
|  | post-SDR material | Triton X-100 | 7.9 |
|  |  | TnBP | <0.3 |
| 9 | pre-SDR material | Triton X-100 | 8142 |
|  |  | TnBP | 2437 |
|  | post-SDR material | Triton X-100 | 14.9 |
|  |  | TnBP | <0.3 |

It was concluded that, advantageously, carrying out an S/D removal in the presence of PVP K25 in a concentration of lower than 1% (0.3 mM) results in increased growth factor recovery during S/D removal step and at the same time ensures efficient S/D removal from the lysate.

Example 13: The Ratio Between Several Growth Factors in a Platelet Extract Prepared from WAP, Treated with S/D, Contacted with PVP K25, and Subjected to S/D Removal The following Example shows the ratio between several growth factors in a platelet extract prepared as disclosed, and examines whether the obtained ratio is comparable to that in the starting material, and to that in the lysate before loading the sample onto the chromatography resin (the pre-SDR material). The pre- and post-SDR material (or extract) were prepared as described in Example 10.

The levels of TGF-$\beta$1, VEGF, bFGF, and PDGF-AB were measured in all three tested materials (WAP starting material, pre-SDR material, and post-SDR material) using the specific commercial ELISA kit described above, and the ratios between PDGF-AB/TGF-$\beta$1; PDGF-AB/VEGF; TGF-$\beta$1/bFGF; and VEGF/bFGF were calculated. The growth factors levels and ratios are shown in Table 13 and 14, respectively, below.

TABLE 13

Levels of TGF-$\beta$1, VEGF, bFGF, and PDGF-AB in WAP starting material, pre-SDR material, and post-SDR material.

| Tested material | Growth factor level (ng) | | | |
|---|---|---|---|---|
|  | TGF-$\beta$1 | VEGF | bFGF | PDGF-AB |
| WAP starting material | 301445 | 2965 | 267 | 119520 |
| Pre-SDR material | 299228 | 2396 | 240 | 102308 |
| Post-SDR material | 249563 | 1818 | 147 | 74365 |

TABLE 14

Calculated growth factor ratio in WAP starting material, pre-SDR material, and post-SDR material.

| Tested material | PDGF-AB/ TGF-β1 | PDGF-AB/ VEGF | TGF-β1/ bFGF | VEGF/ bFGF |
|---|---|---|---|---|
| WAP starting material | 0.40 | 40 | 1129 | 11 |
| pre-SDR material | 0.34 | 43 | 1247 | 10 |
| post-SDR material | 0.30 | 41 | 1698 | 12.4 |

The results show that a platelet lysate contacted with PVP K25 in combination with ethanol and NaCl during a S/D removal step results in an extract having PDGF-AB/TGF-β1; PDGF-AB/VEGF; TGF-β1/bFGF; and VEGF/bFGF ratios which are similar to the ratios in the starting material and in the material prior to S/D removal.

It can be concluded that carrying out an S/D removal as disclosed results in a platelet extract comprising a proportion of factors that is similar to the material before S/D removal.

Example 14: Growth Factor Recovery in Platelet Extracts Prepared by Contacting the Lysate with Heparin, Dextran Sulfate or PVP K25 Prior to and/or During the S/D Removal Step The following Example compares the growth factor recovery in different platelet extracts prepared by contacting the lysate with heparin, dextran sulfate or PVP during the S/D removal step. The recovery was calculated as elaborated above. A platelet extract with heparin was prepared using 1900-2500 g pooled washed apheresis platelets leukocyte reduced (WAP) obtained from 10-13 bags. 209-385 ml acetate-glycine buffer was added to a final concentration of 20 mM sodium acetate, 10 mM glycine; at pH 6.8-7.4 and 0.2% w/w (final concentration) Human serum albumin (HSA, Talecris USA) were added into the pooled WAP. S/D treatment was carried out by slowly adding 1% Triton X-100 and 0.3% TnBP (w/w) into the pooled sample while mixing at 50 RPM. First, the sample was continuously stirred for 30 minutes, and then filtered consecutively through 20 and 3 μm Sartopure PP2 filters and 0.45 μm Sartopore 2 (Sartorius Stedim Biotech S.A., Aubagne, France). Then, the filtered material was returned to a beaker immersed in a water bath adjusted to 25° C. and mixed at 50 RPM for additional 2 hours for continuing the viral inactivation process. S/D removal was carried out using XK50 liquid chromatography column packed with 295 ml SDR HyperD solvent-detergent removal chromatography resin (Pall Corp) in conjunction with a peristaltic pump and a UA-6 UW/WIS detector+Type 11 recorder (ISCO, NE, USA). Equilibration was carried out with the respective buffer of the loaded sample. 1800 ml of S/D-treated platelet lysate (which contained 1620 ml of platelet material) were loaded onto the column followed by washing with 600 ml acetate glycine buffer (same concentrations as above)+0.2% HSA. 600 ml of acetate glycine buffer (same concentrations as above) containing 12.5% ethanol, 0.5M NaCl, 5 IU/ml Heparin (Heparin Sodium-Fresenium 5000 IU/ml. Bodene (PTY) Ltd, South Africa) and 0.2% HSA. This was followed by a second washing step carried out with 600 ml of acetate glycine buffer (same concentrations as above) containing 10% ethanol, 1M NaCl and 0.2% HSA. The column was finally washed with 300 ml of purified water. The flow-through and all fractions obtained in the washing steps were collected and pooled (about 3.6 liter). The collected material was filtered using consecutively 3 and 1.2 μm Sartopure PP2 filters and 0.45 μm Sartopore 2 (Sartorius Stedim Biotech S.A., Aubagne, France).

A platelet extract with dextran sulfate was prepared using 1800-2050 g pooled washed apheresis platelets leukocyte reduced (WAP) obtained from 10 bags. 197-224 ml acetate-glycine buffer was added to a final concentration of 20 mM sodium acetate, 10 mM glycine; at pH 6.8-7.4 and 0.2% w/w (from the final volume solution) Human serum albumin (HSA, Talecris USA) were added into the pooled WAP. S/D treatment was carried out by slowly adding 1% Triton X-100 and 0.3% TnBP (w/w) into the pooled sample while mixing at 50 RPM. In order to avoid sub-optimal viral inactivation due to the possible presence of particulate matter, the S/D treatment was split into two parts. First, the sample was continuously stirred for 30 minutes and then filtered through 20 and 3 μm Sartopure PP2 filters and 0.45 μm Sartopore 2 (Sartorius Stedim Biotech S.A., Aubagne, France). Then, the filtered material was returned to a beaker, immersed in a water bath adjusted to 25° C. and mixed at 50 RPM for additional 2 hours for continuing the viral inactivation process.

Dextran sulfate (Sigma-Aldrich. Canada; Cat. number D4911) was added to the sample to a final concentration of 1% (w/w) and incubated at 25° C. while stirring at 50 RPM for 20 minutes. The sample was filtered using 5 μm Sartopore PP2 filter to remove particulate matter.

Next, S/D removal was carried out using XK50 liquid chromatography column packed with 295 ml SDR HyperD solvent-detergent removal chromatography resin (Pall Corp) in conjunction with a peristaltic pump and a UA-6 UW/WIS detector+Type 11 recorder (ISCO, NE, USA). The column was equilibrated with 900 ml of acetate glycine buffer containing 1% dextran sulfate and 0.2% HSA. 1800 ml of S/D- and dextran sulfate-treated platelet lysate (which contained 1620 ml of platelet material) were loaded onto the column followed by washing with 600 ml acetate-glycine buffer (same concentrations as above) with 12.5% ethanol, 0.5M NaCl, 0.1% dextran sulfate and 0.2% HSA. This was followed by washing with 600 ml of acetate-glycine buffer (same concentrations as above) containing 1% dextran sulfate and 0.2% HSA. Next, the column was washed with 300 ml of purified water. A total volume of 3000 ml was collected from the column. The collected material was filtered using 3 and 1.2 μm Sartopure PP2 filters and 0.45 μm Sartopore 2 (Sartorius Stedim Biotech S.A., Aubagne, France).

A platelet extract with PVP was prepared as elaborated in Example 10.

The comparative growth factor recovery is shown in Table 15 below.

TABLE 15

Growth factor recovery of the different extracts.

| | Growth factor Recovery (%)*** | | |
|---|---|---|---|
| | Extract-Heparin (Average ± SD)* | Extract-Dextran Sulfate (Average ± SD)** | Extract-PVP K25 |
| TGF-β1 | 91 ± 8 | 74 ± 5 | 83 |
| PDGF-AB | 43 ± 5 | 61 ± 10 | 73 |
| PDGF-BB | 69 ± 9 | 65 ± 5 | 87 |

TABLE 15-continued

Growth factor recovery of the different extracts.

Growth factor Recovery (%)***

| | Extract-Heparin (Average ± SD)* | Extract-Dextran Sulfate (Average ± SD)** | Extract-PVP K25 |
|---|---|---|---|
| bFGF | 56 ± 10 | 44 ± 10 | 61 |
| EGF | 56 ± 3 | 52 ± 5 | 59 |
| VEGF | 78 ± 7 | 83 ± 12 | 76 |

*An average between 4 independent extract preparations.
**An average between 6 independent extract preparations.
***% relative to the pre-SDR material.

The results show that preparing an extract contacting with PVP K25 during the S/D removal step resulted in a similar and, with regards to some growth factors, even superior (e.g. PDGF-AB and PDGF-BB) growth factor recovery compared to contacting the lysate with dextran sulfate or heparin.

Advantageously, a platelet extract comprising PVP has no inhibitory effect on thrombin activity in-vitro as compared to heparin (shown in the Examples above) and dextran sulfate at certain concentrations (data not shown).

Example 15: The Effect of a Platelet Extract Prepared as Disclosed on Skin Healing in an In-Vivo Model Tissue ischemia due to compromised blood flow is a major contributor to surgical skin flap failure.

In this experiment, a modified McFarlane rat pedicle skin flap model was used (McFarlane et al., Plast Reconst Surg (1965) 35:177) to evaluate the ability of a platelet extract prepared as disclosed in promoting flap healing.

16 male Spargue-Dawley rats weighing 350-450 g (n=4 per treatment group) were used in this study.

Surgical Procedure:

The dorsal hair was removed one day prior to surgery to uncover the skin. On the day of surgery, animals received pre-operative analgesic in the form of one dose of buprenorphine SQ injection (0.05 mg/Kg), and pre-operative antibiotics (Enrofloxacin: 10 mg/Kg). Anesthesia was administered by isoflurane inhalation (about 1-4%). The surgical site was prepared using chlorohexidine gluconate and 70% isopropyl alcohol. A three-sided rectangular shaped dorsal full thickness flap in the size of about 10×3 cm was created. The flap margins were incised on three sides (cranially to caudally) leaving the flap attached along the caudal edge. The flap was elevated by blunt dissection and the exposed underlying dorsal surface of the flap was progressively drip-coated with 1.5 ml of fibrin sealant (prepared from a BAC2 component comprising a final concentration of 3 mg/ml human fibrinogen, and a final concentration of 250 IU/ml human thrombin) with: i) an extract comprising PVP, ii) an extract comprising heparin or iii) Water for Injection (WFI; as control I). See preparation of the extract and of the administered material and the exact application procedure below. The flap was put back into its anatomical place as the sealant was applied.

The skin flap was repositioned to its correct anatomic location, approximating the edges of the skin surrounding the flap and avoiding dead space by applying gentle pressure during the initial time period required for the sealant to react and form a gel-like consistency. The flap incision was then sutured back in its correct anatomic location using a 4-0 non-absorbable monofilament suture material in a consistent simple interrupted pattern.

A control group (referred to as "control II") underwent the same flap creation procedure, but did not have any treatment applied to the underlying dorsal surface prior to flap closure.

Extract Preparation:

Two platelet extract preparations were examined: one comprising PVP (prepared as in Example 10 PVP); and the other comprising heparin (prepared as in Example 14). Both extracts were then subjected to a step of stabilization, pasteurization and removal of the stabilizers by diafiltration against acetate-glycine buffer as follows:

One gram sucrose per gram of sample was slowly added into the extract material while mixing (at about 22° C.) until the sucrose was completely dissolved. Then, the solution was warmed to 37±1° C. and 0.11 g glycine per g of extract material was slowly added into the solution while mixing and adjusting the pH to 6.8-7.4 using 0.5N NaOH. pH adjustment was carried out until the glycine was completely dissolved. This was followed by a gradual addition of 0.8 g sucrose per g extract material while mixing at 37° C. until completely dissolved. Sucrose and glycine were added into the solution to serve as stabilizers during the pasteurization step. The solution was then pasteurized by heat treatment at 60° C. for 10 hours with constant mixing (50 RPM). In order to transfer the resulting viscous solution (which was formed as a result of the stabilizers addition) into a clean vessel, it was diluted with acetate-glycine buffer (20 mM sodium acetate, and 10 mM glycine at pH 6.8-7.4) up to a total weight of 14,000-14,300 g (about 12,000 ml). The stabilizers were removed from the solution by diafiltration against acetate-glycine buffer (20 mM sodium acetate, 10 mM glycine, pH 6.8-7.4) using Centramate System with 2 Omega 10 kDa cassettes (Pall Corp, Port Washington, N.Y., USA). The diafiltration step was carried out as follows: the sample was first concentrated to a volume of 1800 ml, and dialysis was carried out against a total volume of 10,800 ml acetate-glycine buffer (20 mM sodium acetate, 10 mM glycine, pH 6.8-7.4) by a gradual addition of the buffer and keeping the solution volume at 1,800±200 ml. The dialyzed solution was then concentrated to 410-445 ml.

For stabilization, Mannitol was added into the solution at a final concentration of 2% w/w. In order to remove aggregated material, the solution was filtered through 1.2 μm Sartopure PP2 filter and 0.45 μm Sartopore 2 filter. Sterile filtration was carried out under aseptic conditions using a 0.2 μm Sartopore 2 filter.

The obtained solution was then aliquoted into 4 ml portions into autoclaved glass vials, lyophilized and sealed with autoclaved rubber stoppers under nitrogen atmosphere and in partial vacuum (0.6 Bar).

Preparation of BAC2 (Fibrinogen Comprising Component)+Extract:

The lyophilized extract's vial cap was aseptically opened and 1 ml of sterile Water for Injection (WFI) was slowly added (without pipetting up or down or vortexing as to not create foaming) to the vial of lyophilized extract. The cap was aseptically replaced back on the vial and the vial was placed on a tube roller/rocker for approximately 5 minutes at room temperature or until the extract powder became fully reconstituted.

Next, 2 ml BAC2 (fibrinogen component of EVICEL® fibrin sealant: Omrix Biopharmaceuticals Ltd.;

comprising 60 mg fibrinogen/ml as in EVICEL®) was aseptically mixed with 18 ml BAC2 dilution buffer (to make 6 mg fibrinogen/ml) containing 120 mM sodium chloride, 10 mM tri-sodium citrate, 120 mM glycine, 95 mM arginine hydrochloride, 1 mM calcium chloride, pH-7.0-7.2. The vial was gently agitated for at least 5 minutes. Then, 2 ml diluted BAC2 (6 mg fibrinogen/ml) was drawn into a syringe without a needle and mixed with the above mentioned 1 ml rehydrated extract-heparin; extract-PVP or WFI. The vials were placed on a tube roller/rocker for approximately 5 minutes at room temperature until use.

Preparation and Application of the Tested Article:

The yellow triple lumen catheter tip of the EVICEL® application device was cut at its base and replaced with a 16 G single lumen Venflon™ Intravenous Catheter (without the needle) or other appropriately sized catheter. The vial connectors and the syringes were removed from the device. One of the 3 ml syringes was replaced with a 1 ml syringe, and 1 ml of thrombin component (EVICEL fibrin sealant; Omrix Biopharmaceuticals Ltd.) was aseptically drawn up straight from the vial and into the 1 ml syringe. Three ml of BAC2+a platelet extract comprising heparin; BAC2+a platelet extract comprising PVP; or BAC2+WFI (prepared as described above) were aseptically drawn up into the 3 ml syringe.

The two syringes (one containing 1 ml thrombin; and the other containing 3 ml of BAC2 and extract or WFI solution were placed in the blue barreled syringe holder (from a new EVICEL® application kit) and the provided plastic blue end connector was placed over the ends of both plungers such that both thrombin and the tested solution could be administered simultaneously. As mentioned above, a total volume of 1.5 ml fibrin sealant with: i) an extract comprising PVP, ii) an extract comprising heparin or iii) Water for Injection (WFI: as control 1) was administered in a volume ratio of 3 (fibrinogen comprising component with or without extract):1 (thrombin component) [1.125 ml:0.375 ml].

The growth factor concentration per ml (measured using the ELISA kit described above) in the material administered to the rat was as shown in Table 16 (a volume of 1.5 ml was administered).

TABLE 16

Growth factor concentration in the tested extracts.

| | Growth factor (pg/ml) | | | | |
|---|---|---|---|---|---|
| | TGF-β1 | PDGF-AB | PDGF-BB | VEGF | EGF |
| Extract-Heparin | 217502 | 4555 | 1323 | 1147 | 3777 |
| Extract-PVP | 211153 | 7417 | 1279 | 1844 | 3790 |

Evaluation: At 14 days after surgery the animals were anesthetized, and then euthanized by exposure to $CO_2$. The adherence of a healthy (non-necrotic and soft tissue) area of the flap to the underlying tissue was evaluated according to the following ranking (from worse to best): 1—no flap adherence; 2—partial adherence; and 3—near normal or normal flap adherence.

The scoring/grade for the various treatment groups are shown in Table 17.

TABLE 17

Adherence grade for normal appearing area of the skin flap (scale of 1-3) for the various treatment groups.

| | Adherence grade for normal appearing area of the skin flap (scale of 1-3) | | | |
|---|---|---|---|---|
| Animal | Control II | FS* alone | FS* + a platelet extract comprising heparin | FS + a platelet, extract comprising PVP |
| 1 | 2 | 2 | 3 | 3 |
| 2 | 2 | 2 | 3 | 3 |
| 3 | 2 | 2 | 3 | 3 |
| 4 | 2 | 1 | 2 | 3 |
| AVERAGE | 2 | 1.75 | 2.75 | 3 |

*FS - fibrin sealant.

The results show that administering fibrin sealant in combination with a platelet extract comprising PVP had a similar positive effect in promoting skin flap adherence as administering the fibrin sealant with a platelet extract comprising heparin, both were superior to FS alone or Control II.

Once the macroscopic evaluation was completed, the skin flaps were collected including about 0.5 cm of normal skin adjacent to the lateral edges. The abdominal and thoracic viscera were removed through ventral midline incision. The collected tissue was placed into 10% neutral buffered formalin. After adequate fixation, tissue sections were taken approximately every 2 cm starting from the caudal end and designated as areas A-E, as shown in FIG. 6, perpendicular to the right side of the skin flap in such a manner that normal tissue and the skin flap were included in each tissue section. The tissue sections were processed (infiltrated and embedded in paraffin) and the paraffin blocks were then sectioned using a microtome (5 micron). The sections were mounted on Super Frost+™ slides, and assessed by histology and immunohistochemistry.

Hematoxylin & Eosin staining: Paraffin embedded skin/wound-section slides were incubated at 60° C. for 30 minutes and deparaffinized by washing the slides twice with xylene (100%) for 5 minutes, followed by rehydration in decreasing concentrations of ethanol in DDW (100-70%) for 5 minutes in each concentration. The slides were stained with hematoxylin (ready for use solution) for 8 minutes, rinsed with water, immersed for a few seconds in 1% HCl/70% ethanol and then stained with eosin (0.5% in DDW) for 6 minutes. The sections were then washed with 70% ethanol by 2 quick immersions. Thereafter, the slides were dehydrated by washing once with 95% ethanol for 5 minutes, twice with absolute ethanol for 5 minutes, and twice with xylene (100%) for 3 minutes and then mounted with Entellan mounting medium (MERCK Darmstadt Germany).

Immunohistochemistry staining: Paraffin embedded skin incision section slides were prepared as described above. The slides were incubated with blocking solution (10% normal serum) for 1 hour followed by incubation with one of the following primary antibody: directed against keratin 6, keratin 1, keratin 14 (Covance), PCNA (Santa Cruz) overnight at 4° C. The next day, slides were washed with 0.05% Tween in PBS and incubated with the corresponding secondary biotin-conjugated antibody (Vector Labs) for 1 h. Detection was carried out using ABC Elite kit (Vector Labs), following manufacture instructions. Slides were then rinsed with water, counter-stained with Mayer's hematoxylin for 30 seconds, and then washed with 70% ethanol by 2 quick immersions. Thereafter, the slides were dehydrated by washing once with 95% ethanol for 5 minutes, twice with absolute ethanol for 5 minutes, and twice with xylene (100%) for 10 minutes, then mounted with Entellan mounting medium (MERCK Darmstadt Germany).

Analysis Criteria.

Epidermal hyperplasia: Hyperplastic response as measured by epidermal thickness was determined by H&E staining, where a sample was scored as one, when its epidermal thickness was observed in at least one field to contain >6 nucleated layers. Samples where 6 or less layers were observed on the entire section were scored as zero.

Dermal hyperproliferation: Hyper-proliferative granulation tissue was assessed utilizing PCNA staining of proliferating nuclei, where score 1 was assigned when >10 nuclei per field (×40) were counted at the dermal incision area. Score 0 was assigned when 10 or less nuclei were counted.

Suprabasal keratin 6: Suprabasal keratin 6 was scored 1 when wounds displayed extensive distribution of K6 staining presented by brown staining.

Suprabasal proliferation: Non healed wounds display proliferating cells in several layers above the basal layer at the wound gap, observed by PCNA staining. When suprabasal proliferation was observed in at least one area of the sample, it was scored as 1. Upon advanced healing, proliferation is observed only at the basal layer, which was scored as 0. Taken together, for all markers, a score of zero represents a more advanced healing stage relative to score 1.

FIG. 7 shows representative stainings for the four tested markers from this study. Epidermal hyperplasia, dermal hyperproliferation, suprabasal keratin 6 staining and suprabasal proliferation (left panel) were scored as 1. Representative fields are presented for H&E staining (epidermal hyperplasia), PCNA staining (dermal and epidermal proliferation) and Keratin 6 staining. Yellow arrows in the epidermal hyperplasia panel portray epidermal thickness. Yellow arrows in the K6 panel indicated K6 keratin distribution as presented in brown staining. Red arrows demonstrate PCNA positive nuclei of proliferating cells.

As shown in Table 18, flaps treated with FS+PEX-PVP showed more advanced healing i.e. more animals scored 0 (for definition of scores 0 and 1, see "Methods"), than sham- or FS-treated flaps for 4 different healing markers. FS+PEX-PVP treated wounds displayed a significant reduction in several characteristics of active wounds which included reduction in epidermal hyperplasia, reduction of dermal fibroblast and epidermal keratinocyte proliferation and diminished Keratin 6 staining. Reduced hyperplasia represents the thinning of the epidermis characteristic to normal skin. Reduction of dermal fibroblast and suprabasal keratinocyte proliferation (shown by PCNA staining) marks mature matrix and remodeling of the dermis and epidermis, and reduced Keratin 6 staining limited to a single cell layer at the basal epidermis marks normalization of skin characteristics. In contrast, control (FS) treated rat flaps displayed an early immature healing stage

TABLE 18

Comparison of healing markers in PEX-PVP vs. control treatments in a rat dorsal flap model.

|  | Area | Sham | FS Control | FS + PEX-PVP |
| --- | --- | --- | --- | --- |
| Epidermal Hyperplasia | A | 2/4 | 2/4 | 0/4 |
|  | C | 2/4 | 3/4 | 0/4 |
| Dermal hyperproliferation | C | 2/4 | 2/4 | 1/4 |
|  | D | 3/4 | 3/4 | 2/4 |

TABLE 18-continued

Comparison of healing markers in PEX-PVP vs. control treatments in a rat dorsal flap model.

|  | Area | Sham | FS Control | FS + PEX-PVP |
| --- | --- | --- | --- | --- |
| Suprabasal proliferation | A | 2/4 | 3/4 | 0/4 |
| Suprabasal | A | 1/4 | 2/4 | 0/4 |
| Keratin 6 | C | 2/4 | 3/4 | 1/4 |

Example 16: Large Scale Process of Platelet Lysate Preparation from Pooled Washed Aphaeresis Platelets, Leukocyte Reduced (WAP), Treated with S/D, Incubated with PVP K12, Subjected to SDR Column at the Presence of PVP K12, Treated with Stabilizers, Concentrated with Ultrafiltration/Diafiltration (UF/DF) System and Lyophilized In this experiment, the effect of PVP K12 addition during S/D removal on the recovery of growth factors was evaluated in a large scale process (see example 10). Lower molecular weight (LMW)-PVP, e.g. PVP K12, is more suitable for formulation of parenteral drugs than higher molecular weight PVPs (PVP 25), since the first permits rapid renal elimination without storage. Also, in some countries in Europe, e.g. Germany and Austria, only such low-molecular PVP types with a K-value of up to 18 are approved for injection. Platelet lysate samples were prepared using 1958 g pooled washed apheresis platelet leukocyte reduced (WAP) obtained from 10 bags. 214 ml acetate-glycine final concentration of 20 mM sodium acetate, 10 mM glycine; at pH 6.8-7.4 (AGA buffer) and Human Serum Albumin (HSA; Talecris USA, final concentration of 0.2% v/v) were added into the pooled WAP. In the next step, S/D treatment was carried out by slowly adding Triton X-100 and TnBP 1% and 0.3% (v/v) final concentration, respectively) while mixing at 30 RPM. In order to avoid potential sub-optimal viral inactivation due to the possible presence of particulate matter, the S/D treatment was split into two steps. First, the sample was continuously stirred for 30 minutes, centrifuged at 5016×g for 10 minutes at 23-27° C. and filtered through a 0.45 µm filter (Sartopore 2, Sartorius Stedim Biotech S.A., Aubagne, France). Then, the filtered material was poured into a stainless steel pot immersed in a water bath adjusted to 25° C. and mixed at 30 RPM for additional 2 hours to continue the viral inactivation process in a clear solution. PVP K12 (Polyvinylpyrrolidone K12 with a K-Value of 12 and an average molecular weight of 3500 Da, Cat. 276142500 Acros organics. Germany) was added to the S/D-treated lysate to a final concentration of 0.3% (w/w) i.e. 0.857 mM) and incubated for 20 minutes at 25° C. while stirring at 30 RPM. The sample was filtered using 5 µm Sartopore PP2 filter to remove particulate matter.

Next, S/D removal was carried out on a XK50 liquid chromatography column packed with 300 ml SDR HyperD solvent-detergent removal chromatography resin (Pall Corp) in conjunction with a peristaltic pump and a UA-6 UV/VIS detector+Type 11 recorder (ISCO, NE, USA). The column was equilibrated with 900 ml of AGA buffer (as above) containing 0.3% (0.857 mM) PVP K12. 1800 ml of S/D- and PVP-treated platelet lysate (which contained 1620 ml of platelet material) were loaded onto the column followed by washing the column with 600 ml AGA buffer (as above) containing 0.3% (0.857 mM) PVP K12. This was followed by washing with 600 ml of AGA buffer containing 12.5% ethanol, 1M NaCl and 0.3% (0.857 mM) PVP K12. Flow-through and washing fractions were collected and combined for growth factor recovery calculations.

A total volume of 3000 ml was collected from the column. The collected material was filtered consecutively with 3 and 1.2 µm Sartopure PP2 filters and 0.45 µm Sartopore 2 filter (Sartorius Stedim Biotech S.A., Aubagne, France).

PDGF-AB, PDGF-BB, VEGF, TGF-031, EGF and bFGF recoveries were calculated as described above and are shown in Table 19 below.

TABLE 19

Comparison between recoveries of growth factors in a platelet lysate following S/D removal step in the presence of (PVP K12 or PVP K25).

| | Growth factor Recovery (%)* | |
|---|---|---|
| | Lysate-PVP K25 (0.1 [0.03 mM]-0.5%[0.17 nM])** | Lysate-PVP K12 (0.3%(0.857 mM)) |
| TGF-b1 | 83 | 65 |
| PDGF-AB | 73 | 75 |
| PDGF-BB | 87 | 73 |
| EGF | 59 | 60 |
| bFGF | 61 | 74 |
| VEGF | 76 | 96 |

*Compared to pre-SD step
**For detailed conditions, see example 10.

The results presented in Table 19 show that the high recoveries of growth factors from the SDR column in the presence of PVP K25 are maintained when using lower molecular weight PVP e.g. PVP K12.

Next, the filtered material was poured into a stainless steel pot immersed in a water bath adjusted to 25° C. and mixed at 30 RPM. In preparation for viral heat inactivation, a stabilizing procedure was carried out in three steps. First, 100% sucrose (w/w) was added to the material in small portions. Once the sucrose was completely dissolved, the solution was warmed to 37° C., and 10% glycine (w/w) was slowly added at pH 6.9-7.1. In the last step of stabilizer addition, 80% sucrose (w/w) was added and further mixed until completely dissolved. Then, the heat viral inactivation step was carried out at 59.5-60.5° C. for 10 hours while stirring at 20 RPM.

At the end of the viral inactivation step, 40% acetate-glycine buffer (w/w) was added to the solution while mixing at 37° C. at 30 RPM. The solution was then filtered using 3 µm Sartopure PP2 filter (Sartorius Stedim Biotech S.A., Aubagne, France). Next, concentration and stabilizers removal procedures were carried out using Centramate™ UF Holder system installed with 4 Omega™ Centramate™ 10 kDa cassettes (Pall corp) in 3 steps. First, the material was concentrated to a final volume of 1800 ml. In the second step, 10800 ml of acetate-glycine buffer were gradually added while maintaining the volume of the solution between 1600 to 2000 ml in order to replace the stabilizing buffer with a fresh buffer. Third, at the end of the dialysis step, the sample was concentrated to a final volume of 560 ml.

Mannitol (Sigma-Aldrich, St. Louis, Mo., USA) was added to the material to a final concentration of 2% (w/w). Next, the material was filtered using consecutively 1.2 µm Sartopure 300 filter, 0.45 µm Sartopore 2 filter and 0.2 µm Sartopore 2 300 filter (Sartorius Stedim Biotech S.A., Aubagne, France). 80 glass vials were then filled with 4 ml of the solution and freeze-dried using Epsilon 2-8D lyophilizer (Martin Christ GmbH).

The concentrations of Triton X-100 and TnBP were measured prior to (pre-SDR material) and after the S/D removal step (post-SDR material) and at the end of the production process (Final). Triton X-100 was determined by reversed phase HPLC with a U.V. detector, and TnBP was determined by capillary gas chromatography using a Flame Ionization Detector.

The results are shown in Table 20 below.

TABLE 20

S/D concentration in the lysate prior to, following S/D removal and at the end of the production process according to the conditions elaborated above.

| Material | S/D | ppm |
|---|---|---|
| pre-SDR material | Triton X-100 | 8,795 |
| | TnBP | 2,526 |
| post-SDR material | Triton X-100 | 170 |
| | TnBP | <0.3 |
| Final | Triton X-100 | <5 |
| | TnBP | <0.3 |

The results show that carrying out S/D removal in the presence of PVP K12 at a concentration of 0.3% (0.857 mM), which was found to be efficient for growth factor recovery, resulted in efficient removal of TnBP and almost complete removal of Triton X-100 in the post-SDR intermediate (less than 2% of the starting material remained). The traces of Triton X-100 that remained in the material after the column were removed in the downstream process.

Example 17: The Effect of Contacting a Platelet Lysate with PVP with Different Molecular Weights at Different Concentrations During Loading on S/D Removal Column on Growth Factor Recovery The aim of this example was to investigate the effect of PVPs with different molecular weights at different concentrations on growth factors recovery following S/D removal.

In this example different S/D removal conditions were tested such as the addition of four different molecular weight PVPs prior to and during the HIC S/D removal step. The recovery of the following growth factors was examined: PDGF-AB, bFGF, VEGF, and EGF as determined by ELISA.

PVP K12 (Polyvinylpyrrolidone K12 having a K-Value of 12 and an average molecular weight of 3500 Da, Cat. 276142500 Acros organics, Germany), PVP K17 (Polyvinylpyrrolidone K16-18 having an average K-Value of 17 and an average molecular weight of 8000 Da, Cat. 22746500 Acros organics, Germany), PVP K25 and PVP K30 were used in this example.

The lysates were prepared and loaded onto a SDR column as elaborated in Example 5 above. All S/D removal conditions are elaborated in Table 21. Prior to loading, equilibration was carried out using the buffer of the lysate to be loaded. All loaded samples were also incubated with PVP prior to SDR application, in the manner described above. All fractions obtained from the column after loading, and after washing with the wash buffer were collected, combined, and the growth factor recovery was calculated.

Growth factor recovery results (calculated as explained above) are shown in Table 22.

TABLE 21

A detailed description of samples and conditions used during the S/D removal step.

| Treatment | Sample loaded | Washing buffer |
|---|---|---|
| 1 | S/D treated lysate + 0.3 mM PVP K12 | AGA + 0.3 mM PVP K12 |
| 2 | S/D treated lysate + 0.4 mM PVP K12 | AGA + 0.4 mM PVP K12 |
| 3 | S/D treated lysate + 0.9 mM PVP K12 | AGA + 0.9 mM PVP K12 |
| 4 | S/D treated lysate + 1.7 mM PVP K12 | AGA + 1.7 mM PVP K12 |
| 5 | S/D treated lysate + 0.2 mM PVP K17 | AGA + 0.2 mM PVP K17 |
| 6 | S/D treated lysate + 0.3 mM PVP K17 | AGA + 0.3 mM PVP K17 |
| 7 | S/D treated lysate + 0.8 mM PVP K17 | AGA + 0.8 mM PVP K17 |
| 8 | S/D treated lysate + 1.5 mM PVP K17 | AGA + 1.5 mM PVP K17 |
| 9 | S/D treated lysate + 0.2 mM PVP K25 | AGA + 0.2 mM PVP K25 |
| 10 | S/D treated lysate + 0.3 mM PVP K25 | AGA + 0.3 mM PVP K25 |
| 11 | S/D treated lysate + 0.4 mM PVP K25 | AGA + 0.4 mM PVP K25 |
| 12 | S/D treated lysate + 0.1 mM PVP K30 | AGA + 0.1 mM PVP K30 |
| 13 | S/D treated lysate + 0.3 mM PVP K30 | AGA + 0.3 mM PVP K30 |
| 14 | S/D treated lysate + 0.4 mM PVP K30 | AGA + 0.4 mM PVP K30 |

TABLE 22

Recovery of growth factors in a platelet lysate following S/D removal step at the presence of different MW PVPs (conditions in Table 21).

| | | Growth Factor Recovery (%)* | | | |
|---|---|---|---|---|---|
| Treatment | Details | PDGF-AB | bFGF | EGF | VEGF |
| 1 | 0.3 mM PVP K12 | 17 | 28 | 62 | 78 |
| 2 | 0.4 mM PVP K12 | 18 | 31 | 68 | 88 |
| 3 | 0.9 mM PVP K12 | 38 | 83 | 67 | 102 |
| 4 | 1.7 mM PVP K12 | 71 | 96 | 77 | 108 |
| 5 | 0.2 mM PVP K17 | 41 | 52 | 64 | 96 |
| 6 | 0.3 mM PVP K17 | 42 | 62 | 84 | 103 |
| 7 | 0.8 mM PVP K17 | 77 | 95 | 71 | 111 |
| 8 | 1.5 mM PVP K17 | 89 | 123 | 72 | 106 |
| 9 | 0.2 mM PVP K25 | 51 | 68 | 61 | 98 |
| 10 | 0.3 mM PVP K25 | 55 | 83 | 66 | 98 |
| 11 | 0.4 mM PVP K25 | 53 | 102 | 68 | 95 |
| 12 | 0.1 mM PVP K30 | 40 | 45 | 61 | 83 |
| 13 | 0.3 mM PVP K30 | 62 | 91 | 67 | 104 |
| 14 | 0.4 mM PVP K30 | 55 | 89 | 67 | 104 |

*% relative to the pre-SDR column material.

The results show that increasing the concentration of each PVP correlates within creasing growth factors recovery, especially for PDGF-AB and bFGF. Also, increased growth factor recovery is observed with increased molecular weight of PVP at identical molar concentration: For example, using PVP K12, K17, K25 or K30 at 0.3 mM, resulted in PDGF-AB recovery of 17, 42, 55 and 62%, respectively.

In order to evaluate the efficacy of S/D (Triton X-100 and TnBP) removal, the concentrations of Triton X-100 and TnBP were measured prior (pre-SDR material) to and following (post-SDR material) the S/D removal step. Triton X-100 concentration was determined by reversed phase HPLC with a U.V. detector, and TnBP was determined by capillary gas chromatography using a Flame Ionization Detector.

TABLE 23

S/D concentration in the lysate prior to and following S/D removal according to the conditions elaborated above.

| Treatment | Details | | | ppm |
|---|---|---|---|---|
| | Pre-SDR material for treatments 1, 5, 6, 9, 10 | | Triton X-100 | 8228 |
| | | | TnBP | 2750 |
| | Pre-SDR material for treatments 2, 3, 11, 12, 14 | | Triton X-100 | 7936 |
| | | | TnBP | 2168 |
| | Pre-SDR material for treatments 4, 7, 8 | | Triton X-100 | 8095 |
| | | | TnBP | 2374 |
| | Pre-SDR material for treatment 13 | | Triton X-100 | 7350 |
| | | | TnBP | 2181 |
| 1 | 0.3 mM PVP K12 | post-SDR material | Triton X-100 | <5 |
| | | | TnBP | <0.3 |
| 2 | 0.4 mM PVP K12 | post-SDR material | Triton X-100 | 13 |
| | | | TnBP | <0.3 |
| 3 | 0.9 mM PVP K12 | post-SDR material | Triton X-100 | 52 |
| | | | TnBP | <0.3 |
| 4 | 1.7 mM PVP K12 | post-SDR material | Triton X-100 | 173 |
| | | | TnBP | <0.3 |
| 5 | 0.2 mM PVP K17 | post-SDR material | Triton X-100 | <5 |
| | | | TnBP | <0.3 |
| 6 | 0.3 mM PVP K17 | post-SDR material | Triton X-100 | 18 |
| | | | TnBP | <0.3 |
| 7 | 0.8 mM PVP K17 | post-SDR material | Triton X-100 | 39 |
| | | | TnBP | <0.3 |
| 8 | 1.5 mM PVP K17 | post-SDR material | Triton X-100 | 86 |
| | | | TnBP | <0.3 |
| 9 | 0.2 mM PVP K25 | post-SDR material | Triton X-100 | <5 |
| | | | TnBP | <0.3 |
| 10 | 0.3 mM PVP K25 | post-SDR material | Triton X-100 | 7 |
| | | | TnBP | <0.3 |
| 11 | 0.4 mM PVP K25 | post-SDR material | Triton X-100 | 82 |
| | | | TnBP | <0.3 |
| 12 | 0.1 mM PVP K30 | post-SDR material | Triton X-100 | <5 |
| | | | TnBP | <0.3 |
| 13 | 0.3 mM PVP K30 | post-SDR material | Triton X-100 | <5 |
| | | | TnBP | <0.3 |
| 14 | 0.4 mM PVP K30 | post-SDR material | Triton X-100 | 56 |
| | | | TnBP | <0.3 |

The results show an efficient removal of S/D during the S/D removal step by HIC column. While all TnBP is removed, some residuals of Triton X-100 are found in post-SDR material when using PVP in concentrations of 0.4 mM and above. It was shown in Example 16 Table 20 above that residual Triton X-100 in the intermediate material, even slightly higher than the concentrations presented here, was removed downstream to the presented production process.

Example 18: The Effect of Using PVP in Different Stages of S/D Removal on Growth Factor Recovery In order to identify at which stage in the multistep process of PVP application to the S/D removal column PVP's have the greatest effect on recovery of growth factors, different combinations of PVP addition to the three S/D removal steps were tested.

In this example the recovery of GFs during S/D removal step was tested with the addition of 0.5% (w/w) (0.63 mM) PVP K17 to the platelet lysate, to the equilibration buffer and to the washing buffer at different combinations as shown in Table 24.

The recovery of the following growth factors was examined: PDGF-AB, bFGF, VEGF, and EGF using ELISA. The lysates were prepared and loaded onto a SDR column as elaborated in Example 5, in larger scale process above, with the exception of using equilibration and washing buffers in each treatment as shown in Table 24. Flow through and washing fractions o were collected and combined and the growth factor recovery was calculated.

Growth factor recovery results (calculated as explained above) are shown in Table 25.

TABLE 24

A detailed description of samples and conditions used during the S/D removal step.

| Treatment | Sample loaded | Equilibration buffer | Washing buffer |
|---|---|---|---|
| 1 | S/D treated lysate+ | AGA− | AGA− |
| 2 | S/D treated lysate+ | AGA+ | AGA− |
| 3 | S/D treated lysate+ | AGA− | AGA+ |
| 4 | S/D treated lysate+ | AGA+ | AGA+ |
| 5 | S/D treated lysate− | AGA+ | AGA |
| 6 | S/D treated lysate− | AGA+ | AGA+ |
| 7 | S/D treated lysate− | AGA− | AGA+ |

+PVP K17 was added at 0.5% (0.63 mM).
−No addition of PVP K17.
*% relative to the pre-SDR material.

TABLE 25

Recovery of growth factors in a platelet lysate following S/D removal step according to the samples and conditions in Table 24. Results are sorted in a descending order according to PDGF-AB recovery.

| | 0.5% PVP K17 | Growth factor Recovery (%)* | | | |
|---|---|---|---|---|---|
| Treatment | presence | PDGF-AB | bFGF | EGF | VEGF |
| 2 | S/D treated Lysate Equilibration buffer | 74 | 96 | 77 | 133 |
| 4 | S/D treated Lysate Equilibration buffer Washing buffer | 69 | 100 | 76 | 123 |
| 6 | Equilibration buffer Washing buffer | 55 | 75 | 71 | 115 |
| 5 | Equilibration buffer | 38 | 68 | 74 | 105 |
| 1 | S/D treated Lysate | 36 | 59 | 65 | 117 |
| 3 | S/D treated Lysate Washing buffer | 29 | 57 | 67 | 111 |
| 7 | Washing buffer | 21 | 36 | 61 | 103 |

*% relative to pre-SDR material.

In three samples, 0.5% PVP K17 was added only to one step: to the platelet lysate (treatment #1), to the equilibration buffer (treatment #5) or to the washing buffer (treatment #7).

Addition of PVP K17 only to the platelet lysate or to the equilibration buffer resulted in similarly low growth factor recovery, whereas addition of PVP K7 only to the washing buffer resulted in the lowest improvement in GFs recovery, compared with the two other treatments.

Three additional treatments (treatment #2, #3 and #6) included combinations between two of the three conditions while a treatment #4 included a combination of all three conditions.

The results show that the most effective single step in increasing GFs recovery from the HIC column was addition of PVP to the equilibration buffer. Moreover, the highest GFs recovery was achieved using a combination of PVP in the equilibration buffer with addition of PVP to the lysate.

In order to evaluate the efficacy of S/D (Triton X-100 and TnBP) removal, the concentrations of Triton X-100 and TnBP were measured prior (pre-SDR material) to and following (post-SDR material) the S/D removal step. Triton X-100 was determined by reversed phase HPLC with a U.V. detector, and TnBP was determined by capillary gas chromatography using a Flame Ionization Detector.

TABLE 26

S/D concentration in the lysate prior to and following S/D removal according to the conditions elaborated above.

| Treatment | 0.5% (0.63 mM) PVP K17 presence | Material | S/D | ppm |
|---|---|---|---|---|
| | pre-SDR material for treatments 1-4 | | Triton X-100 | 8601 |
| | | | TnBP | 2516 |
| | pre-SDR material for treatments 5-7 | | Triton X-100 | 8322 |
| | | | TnBP | 2564 |
| 2 | Lysate Equilibration buffer | post-SDR material | Triton X-100 | 101 |
| | | | TnBP | <0.3 |
| 4 | Lysate Equilibration buffer Washing buffer | post-SDR material | Triton X-100 | 73 |
| | | | TnBP | <0.3 |
| 6 | Equilibration buffer Washing buffer | post-SDR material | Triton X-100 | 7 |
| | | | TnBP | <0.3 |
| 5 | Equilibration buffer | post-SDR material | Triton X-100 | 30 |
| | | | TnBP | <0.3 |
| 1 | Lysate | post-SDR material | Triton X-100 | <5 |
| | | | TnBP | <0.3 |
| 3 | Lysate Washing buffer | post-SDR material | Triton X-100 | 7 |
| | | | TnBP | <0.3 |
| 7 | Washing buffer | post-SDR material | Triton X-100 | <5 |
| | | | TnBP | <0.3 |

The results show an efficient removal of S/D during the S/D removal step by HIC column. While all TnBP was removed in all treatments, some residuals of Triton X-100 were found in post-SDR material when using PVP both in the equilibration buffer and in the platelet lysate. However, it was shown in example 16 above that higher concentration of Triton X-100 in the intermediate material than the concentrations presented here were removed in the downstream process.

Addition of PVP to the equilibration buffer as well as to the washing buffer resulted in high recovery of growth factors, without significantly compromising the efficacy of triton X-100 removal by the HIC column.

Example 19: The Effect of Admixing a Platelet Lysate with HPMC Prior to S/D Removal on Growth Factor Recovery In order to test if other amphiphilic polymers can be used to improve the recovery of growth factors during the S/D removal step by HIC column, Hydroxy Propyl Methyl Cellulose (HPMC) was explored in the following example.

HPMC is a natural multifunctional carbohydrate polymer currently widely used as an excipient and controlled-delivery component in oral medicaments and as an emulsifier in food industry.

In this example, two different concentrations of HPMC (10 KDa, Cat. 423238 Sigma-Aldrich, USA) were tested prior to and during HIC S/D removal step. S/D removal step without additives was tested as control.

The lysates were prepared and loaded onto a SDR column as elaborated in Example 5 above. In order to investigate the effect of HPMC alone (without NaCl and EtOH), in this example only 1 buffer with volume of 15 ml was used for washing. All the conditions are elaborated in Table 27. Prior to loading, equilibration was carried out using the same buffer as the one used in the lysate loaded. Flow through and washings were collected, combined, and the growth factor recovery was calculated. Growth factor recovery results (calculated as explained above) are shown in Table 28 All loaded samples that comprised HPMC were incubated with HPMC in the manner discussed above.

The recovery of the following growth factors was examined: PDGF-AB, b(basic) FGF, VEGF, and EGF using ELISA.

TABLE 27

A detailed description of samples and conditions used during the S/D removal step.

| Treatment | Sample loaded | Washing Buffer |
|---|---|---|
| 1 | S/D treated lysate | AGA |
| 2 | S/D treated lysate + 0.1% (0.1 mM) HPMC | AGA + 0.1% (0.1 mM) HPMC |
| 3 | S/D treated lysate + 0.3% (0.3 mM) HPMC | AGA + 0.3% (0.3 mM) HPMC |

TABLE 28

Recovery of various growth factors in a platelet extract following S/D removal step according to the samples and conditions in Table 27.

| | Growth factor Recovery (%)* | | | |
|---|---|---|---|---|
| Treatment | PDGF-AB | bFGF | EGF | VEGF |
| 1 | 7 | 13 | 44 | 48 |
| 2 | 22 | 25 | 55 | 66 |
| 3 | 28 | 39 | 63 | 89 |

*% relative to pre-SDR column.

The results show that contacting an S/D-treated platelet lysate with HPMC prior to and during S/D removal by an SDR column improved the recovery of growth factors from an SDR column.

Also, the results show that higher concentration of HPMC during the S/D removal step resulted in increased recovery of growth factors.

The concentrations of Triton X-100 and TnBP were measured prior (pre-SDR material) to and following (post-SDR material) the S/D removal step. Triton X-100 was determined by reversed phase HPLC with a U.V. detector, and TnBP was determined by capillary gas chromatography using a Flame Ionization Detector.

The results are shown in Table 29 below.

TABLE 29

S/D concentration in the lysate prior to and following S/D removal according to the conditions elaborated above.

| Treatment | Material | S/D | ppm |
|---|---|---|---|
| 1 | pre-SDR material | Triton X-100 | 8322 |
| | | TnBP | 2564 |
| | post-SDR material | Triton X-100 | <5 |
| | | TnBP | <0.3 |
| 2 | pre-SDR material | Triton X-100 | 8492 |
| | | TnBP | 2555 |
| | post-SDR material | Triton X-100 | <5 |
| | | TnBP | <0.3 |

TABLE 29-continued

S/D concentration in the lysate prior to and following S/D removal according to the conditions elaborated above.

| Treatment | Material | S/D | ppm |
|---|---|---|---|
| 3 | pre-SDR material | Triton X-100 | 8297 |
| | | TnBP | 2573 |
| | post-SDR material | Triton X-100 | <5 |
| | | TnBP | <0.3 |

The results show that carrying out an S/D material removal in the presence of HPMC in a concentration of up to 0.3%, which was found to be efficient for growth factor recovery, did not affect the S/D removal performance of the column.

TABLE 30

PVP and HPMC concentrations and MW.

| PVP | K-Value | MW average (Dalton) | Conc. (% w/w) | Conc. (mM) |
|---|---|---|---|---|
| K12 | 10.2-13.8 | 3500 | 0.5 | 1.43 |
| K17 | 16.0-18.0 | 8000 | 0.5 | 0.63 |
| K25 | 22.5-27.0 | 30000 | 0.5 | 0.17 |
| K25 | 22.5-27.0 | 30000 | 1 | 0.3 |
| K30 | 27.0-32.4 | 40000 | 0.5 | 0.13 |
| HPMC | — | 10000 | 0.5 | 0.5 |

Example 20: The Ratio Between Several Growth Factors in a Platelet Extract Prepared from WAP, Treated with S/D, Contacted with PVP K12, and Subjected to S/D Removal The following Example shows the ratio between several growth factors in a platelet extract prepared as disclosed, and examines whether the obtained ratio is comparable to that in the starting material, and to that in the lysate before loading the sample onto the chromatography resin (the pre-SDR material). The pre- and post-SDR material (or extract) were prepared as described in Example 16.

The levels of TGF-β1, VEGF, bFGF, and PDGF-AB were measured in all three tested materials (WAP starting material, pre-SDR material, and post-SDR material) using the specific commercial ELISA kit described above, and the ratios between PDGF-AB/TGF-β1; PDGF-AB/VEGF; TGF-β1/bFGF; and VEGF/bFGF were calculated. The growth factors levels and ratios are shown in Table 31 and 32, respectively, below.

TABLE 31

Levels of TGF-β1, VEGF, bFGF, and PDGF-AB in WAP starting material, pre-SDR material, and post-SDR material.

| | Growth factor level (ng) | | | |
|---|---|---|---|---|
| Tested material | TGF-β1 | VEGF | bFGF | PDGF-AB |
| WAP starting material | 318740 | 1368 | 139 | 151810 |
| Pre-SDR material | 462757 | 1226 | 256 | 159791 |
| Post-SDR material | 299010 | 1178 | 189 | 120126 |

TABLE 32

Calculated growth factors ratio in WAP starting material, pre-SDR material, and post-SDR material.

| Tested material | PDGF-AB/ TGF-β1 | PDGF-AB/ VEGF | TGF-β1/ bFGF | VEGF/ bFGF |
|---|---|---|---|---|
| WAP starting material | 0.48 | 111 | 2288 | 9.8 |
| pre-SDR material | 0.34 | 130 | 1810 | 4.8 |
| post-SDR material | 0.40 | 102 | 1582 | 6.2 |

The results show that a platelet lysate contacted with PVP K2 in combination with ethanol and NaCl during a S/D removal step results in an extract having PDGF-AB/TGF-β1; PDGF-AB/VEGF; TGF-β1/bFGF; and VEGF/bFGF ratios which are comparable to the ratios in the starting material and in the material prior to S/D removal. It can be concluded that carrying out an S/D removal as disclosed results in a platelet extract comprising a proportion of factors that is comparable to the material before S/D removal.

What is claimed is:

1. A method for preparing a viral-safe biological liquid mixture composition from a biological source, the method comprising the following steps:
   providing the source as a clear solution;
   providing a non-toxic amphiphilic polymer;
   treating the source with a solvent detergent (S/D) to allow viral inactivation;
   treating the source with the amphiphilic polymer at a final concentration of 0.01 to 0.9 mM wherein the clarity of the solution is maintained;
   removing the S/D by contacting the treated source with an hydrophobic interaction chromatography (HIC) resin; and
   collecting a material comprising an unbound fraction from HIC;
   wherein the method comprises at least one more orthogonal viral inactivation treatment, thereby obtaining the viral-safe biological liquid mixture composition.

2. The method according to claim 1, wherein removing the S/D omits a further step of oil extraction.

3. The method according to claim 1, wherein the HIC resin is packed in a column.

4. The method according to claim 1, wherein the source comprises cells, cell particles and/or cell organelles.

5. The method according to claim 1, wherein the source is a blood buffy coat.

6. The method according to claim 1, wherein the source comprises platelets.

7. The method according to claim 1, wherein the source is a platelet-enriched fraction pooled from multiple donors.

8. The method according to claim 1, wherein the amphiphilic polymer is a hydrocarbon based surfactant.

9. The method according to claim 1, wherein the amphiphilic polymer is selected from the group consisting of polyvinylpyrrolidone (PVP), hydroxy propylmethylcellulose (HPMC), and a combination thereof.

10. The method according to claim 9, wherein the source is contacted first with the S/D and then with the PVP and wherein the PVP concentration in the S/D treated source is in the range of about 0.01 to 0.3 mM.

11. The method according to claim 9, wherein the source is contacted first with the S/D and then with the PVP and wherein the PVP concentration in the S/D treated source is in the range of about 0.025 to 0.3 mM.

12. The method according to claim 9, wherein the source is contacted first with the S/D and then with the HPMC and wherein the HPMC concentration in the S/D treated source is in the range of about 0.01 to 0.3 mM.

13. The method according to claim 1, wherein the source is contacted first with the S/D and then with the amphiphilic polymer.

14. The method according to claim 1, wherein the method further comprises the steps of: washing the resin with a solution comprising an organic solvent and/or a salt; collecting a fraction obtained following the washing step and combining with the unbound fraction.

15. The method according to claim 14, wherein the organic solvent is ethanol.

16. The method according to claim 14, wherein the salt is NaCL.

17. The method according to claim 1, wherein the at least one more orthogonal viral inactivation treatment comprises heat inactivation.

18. The method according to claim 1, further comprising a step of concentrating the material.

19. The method according to claim 1, further comprising a step of drying the material, thereby resulting in a viral-safe biological dry mixture.

20. A method for preparing a biological liquid mixture composition from a biological source, the method comprising the following steps:
   providing the source as a clear solution;
   providing PVP and/or HPMC;
   treating the source with a solvent detergent (S/D) to allow viral inactivation;
   treating the source with the PVP and/or HPMC at a final concentration of 0.01 to 0.9 mM wherein the clarity of the solution is maintained;
   removing the S/D by contacting the treated source with an hydrophobic interaction chromatography (HIC) resin; and
   collecting a material comprising an unbound fraction from HIC.

21. A method for removing solvent-detergent (S/D) from a biological source comprising S/D, the method comprises the steps of:
   providing the source as a clear solution;
   providing an amphiphilic polymer;
   treating the source with S/D and with the amphiphilic polymer at a final concentration of 0.01 to 0.9 mM wherein the clarity of the solution is maintained;
   removing the S/D from the biological source by contacting the treated source with an hydrophobic interaction chromatography (HIC) resin; and
   collecting a material comprising an unbound fraction from HIC.

22. The method according to claim 21, wherein removing the S/D omits a further step of oil extraction.

* * * * *